(12) United States Patent
Prendergast et al.

(10) Patent No.: US 7,714,139 B2
(45) Date of Patent: May 11, 2010

(54) IDO INHIBITORS AND METHODS OF USE

(75) Inventors: George C. Prendergast, Bala Cynwyd, PA (US); Alexander J. Muller, Media, PA (US); James B. Duhadaway, Wilmington, DE (US); William Malachowski, Collegeville, PA (US)

(73) Assignee: Lankenau Institute for Medcial Research, Wynnewood, PA (US)

( * ) Notice: Subject to any disclaimer, the term of this patent is extended or adjusted under 35 U.S.C. 154(b) by 1003 days.

(21) Appl. No.: 10/550,444

(22) PCT Filed: Feb. 20, 2004

(86) PCT No.: PCT/US2004/005154

§ 371 (c)(1),
(2), (4) Date: Jun. 1, 2006

(87) PCT Pub. No.: WO2004/094409

PCT Pub. Date: Nov. 4, 2004

(65) Prior Publication Data

US 2007/0173524 A1   Jul. 26, 2007

Related U.S. Application Data

(60) Provisional application No. 60/458,162, filed on Mar. 27, 2003, provisional application No. 60/527,449, filed on Dec. 5, 2003.

(51) Int. Cl.
*A61K 31/429* (2006.01)
*C07D 275/00* (2006.01)
(52) U.S. Cl. .................. 548/207; 514/373
(58) Field of Classification Search ............ 548/207
See application file for complete search history.

(56) References Cited

U.S. PATENT DOCUMENTS

| | | |
|---|---|---|
| 2007/0037752 A1 | 2/2007 | Ansorge et al. |
| 2007/0037785 A1 | 2/2007 | Ansorge et al. |
| 2007/0078130 A1 | 4/2007 | Ansorge et al. |
| 2007/0099844 A1 | 5/2007 | Prendergast et al. |

FOREIGN PATENT DOCUMENTS

WO    WO 01/28493    4/2001

WO    2004/093871 A1    11/2004

OTHER PUBLICATIONS

Golub et al., Science, vol. 286, Oct. 15, 1999, pp. 531-537.*
Mehta, Rajendra G. et al., "Cancer chemopreventive activity of brassinin, a phytoalexin from cabbage", Carcinogenesis, 16(2): 399-404 (1995).
Mehta, Rajendra G. et al., "Structure-Activity Relationships of Brassinin in Preventing the Development of Carcinogen-Induced Mammary Lesions in Organ Culture", Anticancer Research, 14: 1209-1214 (1994).
Masuda, M. et al., "Epigallocatechin-3-gallate decreases VEGF production in head and neck and breast carcinoma cells by inhibiting EGPR-related pathways of signal transduction", Journal of Experimental Therapeutics and Oncology, 2(6): 350-359 (2002).
Lin, Jen-Kun, "Cancer chemoprevention by tea polyphenols through modulating signal transduction pathways", Archives of Pharmacal. Reasearch, 25(5), 561-571 (2002) [Abstract].
Cover, C.M. et al., "Indole-3-Carbinol and Tamoxifen Cooperate to Arrest to the Cell Cycle of MCF-7 Human Breast Cancer Cells", Cancer Research, 59: 1244-1251 (1999).
Jakse, R. et al., "A simple synthesis of aplysinopsin analogues by dimethylamine substitution in N,N-(dimethylamino) methylidene derivatives of five-membered heterocycles", Tetrahydron, 57: 8395-8403 (2001).
M. Masuda et al., "Epigallacatechin-3-gallate decreases VEGF production in head and neck and breast carcinoma cells by inhibiting EGPR-related pathways of signal transduction", Journal of Experimental Therapeutics and Oncology, 2: 350-359 (2002).
Lin Jen-Kun, Database BIOSIS, "Cancer chemoprevention by tae polyphenols through modulating signal transduction pathways", Archives of Pharmacal Research (Seoul), 25: 561-571 (2002).
C.M. Cover et al., "Indole-3-Carbinol and Tamoxifen Cooperate to Arrest the Cell Cycle of MDF-7 Human Breast Cancer Cells", Cancer Research, 59: 1244-1251 (1999).
R. Jakse et al., A simple synthesis of aplysinopsin analogues by dimethylamine substitution in N,N-(dimethylamino) methylidene derivatives of five-membered heterocycles, Tetrahydron, 57: 8395-8403 (2001).
Goodman & Gilman's The Pharmacological Basis of Therapeutics, Ninth Edition, pp. 1295-1296 (1996).

* cited by examiner

*Primary Examiner*—Laura L. Stockton
(74) *Attorney, Agent, or Firm*—Patrick J. Hagan; Dann, Dorfman, Herrell and Skillman, P.C.

(57) ABSTRACT

Compounds, compositions and methods for the treatment of malignancy are disclosed.

9 Claims, 31 Drawing Sheets

Scheme 2 Derivatization of Indole at C-4 and N-1

Scheme 3 Synthesis of C-6 Substituted Indoles

Scheme 4 Synthesis of C-4, C-5 and C-6 Trisubstituted Indoles

Scheme 5 Alternative Synthesis of Thiohydantoin Derivatives

Scheme 6 Brassinin Derivative Synthesis

Scheme 7 Synthesis of C-5 and C-6 Substituted β-Carboline Derivatives

Scheme 8 Synthesis of C-3 Alkyl Substituted β-Carboline Derivatives

Scheme 9 Alternative Synthesis of β-Carboline Derivatives

Scheme 10 Synthesis of 3-Amino-6/7-Bromo-2-Naphthoic Acid

Scheme 11 Synthesis of C-6, C-7 and C-8 Trisubstituted 3-Amino-2-Naphthoic Acids Scheme 12 Alternative Synthesis of C-6, C-7 and C-8 Trisubstitute 3-Amino-2-Naphthoic Acids

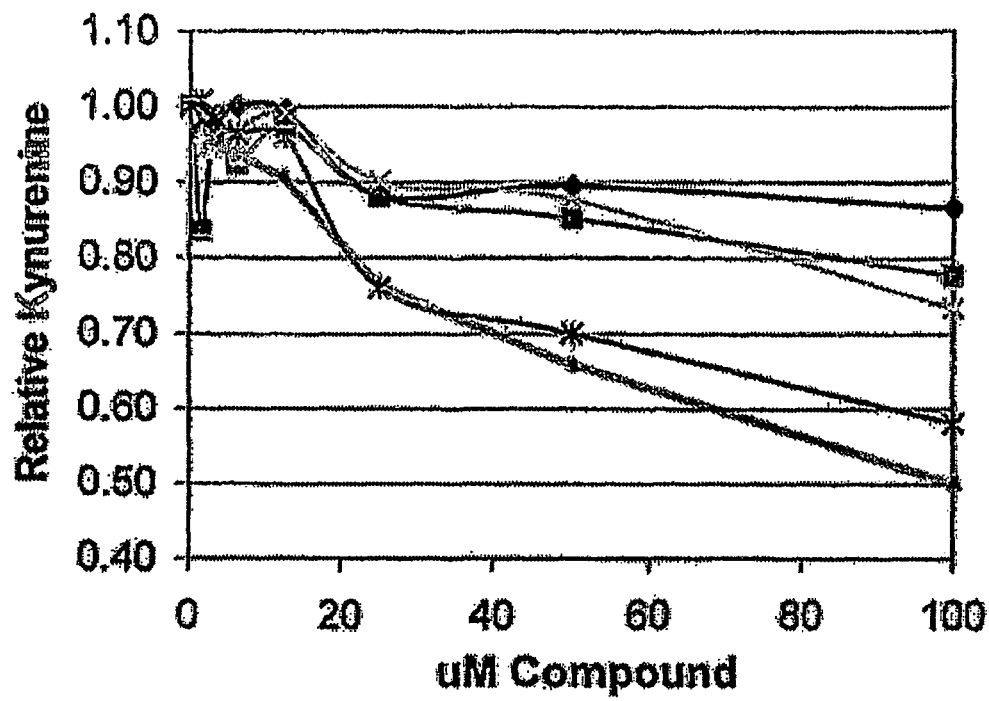
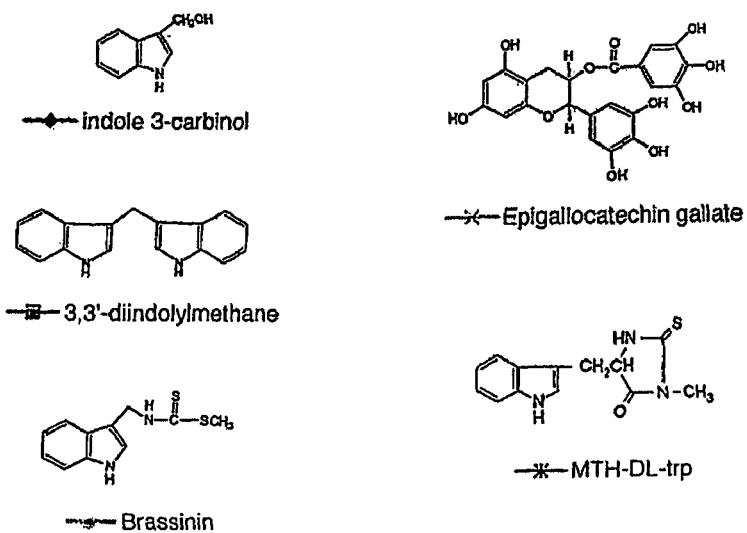
Figure 24

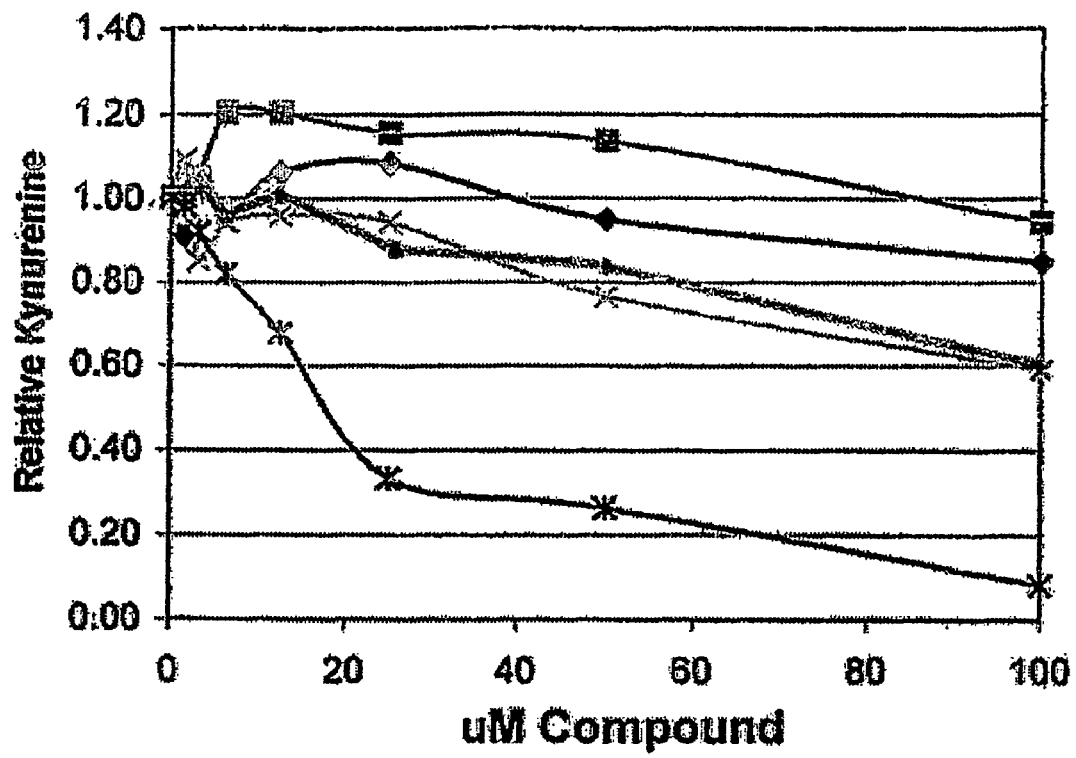
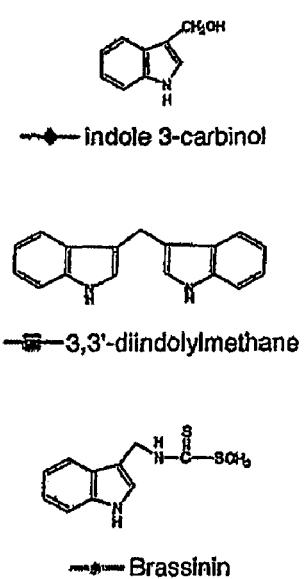
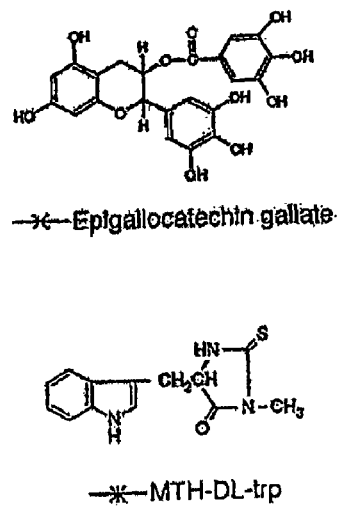
Figure 25A

| Compound name | Structure | IDO inhibition @ 250 µM | TDO inhibition @ 250 µM | Ratio IDO:TDO inhibition |
|---|---|---|---|---|
| 1-DL-Methyl-Tryptophan | 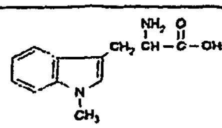 | 25.32% | 4.74% | 5.34 |
| 9-Vinylcarbazole | 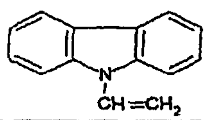 | 22.94% | 19.33% | 1.19 |
| Acemetacin | | 30.25% | N.D. | N.D. |
| 5-Bromo-DL-tryptophan | 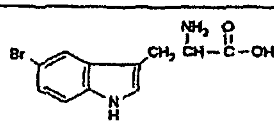 | 31.49% | 18.05% | 1.74 |
| Acemetacin | | 32.65% | 12.44% | 2.62 |
| 5-Bromoindoxyl diacetate | 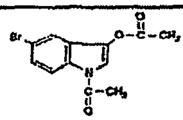 | 69.72% | N.D. | N.D. |

Thiohydantoin (TH) derivatives of indoleamine

| Compound name | Structure | IDO inhibition @ 250 µM | TDO inhibition @ 250 µM | Ratio IDO:TDO inhibition |
|---|---|---|---|---|
| phenyl-TH-DL-trp (PTH-trp) | | 56.95% | 17.83% | 3.19 |
| propenyl-TH-DL-trp (propTH-trp) | | 62.72% | 25.17% | 2.49 |
| methyl-TH-DL-trp (MTH-trp) | | 68.40% | 27.05% | 2.53 |

Figure 27

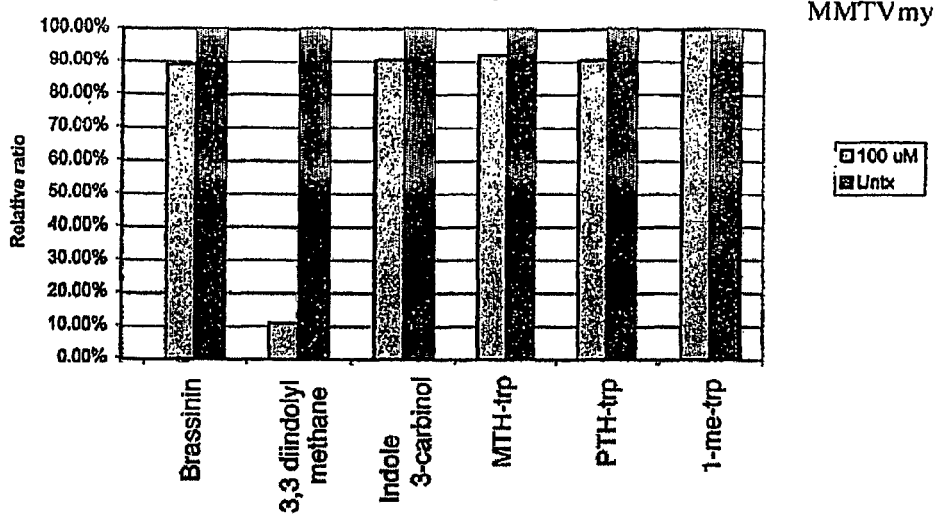
Myc-transformed mouse mammary cells (tumor-derived from MMTVmyc mouse)
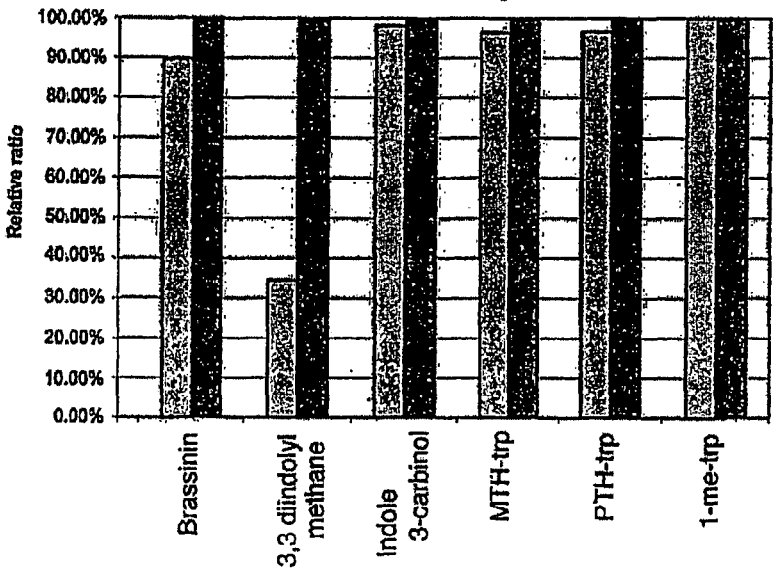
Myc/Ras-transformed p53–/– mouse prostate cells
Figure 28

IDO INHIBITORS AND METHODS OF USE

This application is a 35 U.S.C. §371 application based on PCT/US2004/005154, filed 20 Feb. 2004, which claims the benefit of U.S. Provisional Patent Application 60/458,162 filed 27 Mar. 2003 and U.S. Provisional Patent Application 60/527,449 filed 5 Dec. 2003. The entire disclosure of each of the above identified applications is incorporated by reference herein.

FIELD OF THE INVENTION

This invention relates to the field of oncology. Specifically, the invention provides novel chemotherapeutic agents and methods of using such agents for the treatment of cancer.

BACKGROUND OF THE INVENTION

Tumors characteristically express atypical, potentially immunoreactive antigens that are collectively referred to as tumor antigens. Accumulating evidence suggests that the failure of the immune system to mount an effective response against progressively growing tumors is not attributable to a lack of recognizable tumor antigens. Immunosuppression by tumors is poorly understood and mechanisms by which tumors may escape immune surveillance have been poorly explored. Recently, it has been shown that cytotoxic T cells become tolerized by a reduction in local concentrations of tryptophan that are elicited by indoleamine 2,3-dioxygenase (IDO) activity.

IDO is an oxidoreductase that catalyzes the rate-limiting step in tryptophan catabolism. This enzyme is structurally distinct from tryptophan dioxygenase (TDO), which is responsible for dietary tryptophan catabolism in the liver. IDO is an IFN-γ target gene that has been suggested to play a role in immunomodulation (Mellor and Munn (1999) Immunol. Today, 20:469-473). Elevation of IDO activity depletes the levels of tryptophan in local cellular environments. Induction of IDO in antigen-presenting cells, where IDO is regulated by IFN-γ, blocks the activation of T cells, which are especially sensitive to tryptophan depletion. T cells must undergo 1-2 rounds of cell division to become activated, but in response to tryptophan depletion they arrest in G1 instead. In this way, IDO has been proposed to inhibit the $T_H 1$ responses that promote cytotoxic T cell development.

The main evidence for the role of IDO in immunosuppression is demonstrated by the ability of 1-methyl-tryptophan (1MT), a specific and bioactive IDO inhibitor (Cady and Sono (1991) Arch. Biochem. Biophys. 291:326-333), to elicit MHC-restricted and T cell-mediated rejection of allogeneic mouse concepti (Mellor et al. (2001) Nat. Immunol. 2:64-68; Munn et al. (1998) Science. 281: 1191-93). This effect is consistent with the high levels of IDO expression in placental trophoblast cells (Sedlmayr et al. (2002) Mol. Hum. Reprod. 8:385-391).

Significantly, IDO activity has been shown to be elevated frequently in human tumors and/or in cancer patients (Yasui et al. (1986) Proc. Natl. Acad. Sci. USA. 83:6622-26; Taylor and Feng (1991) FASEB J. 5:2516-22). Since IDO can modulate immune responses, one logical implication is that IDO elevation in cancer may promote tumor immunosuppression (Mellor and Munn (1999) Immunol. Today, 20:469-473; Munn et al. (1999) J. Exp. Med. 189:1363-72; Munn et al. (1998) Science. 281:1191-93). This possibility is supported by the observation that many cancers, including breast cancer, are characterized by a loss of beneficial immune functions that can limit malignant development. For example, $T_H 1$ responses (of which IFN-γ production is a hallmark) that promote the production of cytotoxic T cells are suppressed during cancer progression. A resultant hypothesis from this data was that if IDO drives cancer progression by blunting T cell activation, then IDO inhibition in animals should blunt tumor growth by reversing IDO-mediated immunosuppression. However, delivery of the IDO inhibitor 1-methyl-tryptophan (1MT) only retarded and did not prevent tumor growth in a mouse model (Friberg et al. (2002) Int. J. Cancer 101: 151-155; U.S. Pat. No. 6,482,416).

Cellular signal transduction, i.e., the series of events leading from extracellular events to intracellular sequelae, is an aspect of cellular function in both normal and disease states. Numerous proteins that function as signal transducing molecules have been identified, including receptor and non-receptor tyrosine kinases, phosphatases and other molecules with enzymatic or regulatory activities. These molecules generally demonstrate the capacity to associate specifically with other proteins to form a signaling complex that can alter cellular proliferation.

Aberrant signal transduction can lead to malignant transformation, growth, and progression. Accordingly, inhibitors of signal transduction pathways have been used to treat cancer. During the past few years, a number of signal transduction inhibitors (STIs) have been developed and their ability to suppress tumor growth is currently under investigation.

SUMMARY OF THE INVENTION

In accordance with one aspect of the invention, novel inhibitors of indoleamine 2,3-dioxygenase (IDO) activity are provided. The novel compounds have a formula selected from the group consisting of formula (I):

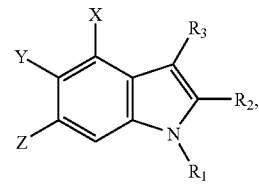

wherein $R_1$ is H or lower alkyl; $R_2$ is H; $R_3$ is selected from the group consisting of: (a)

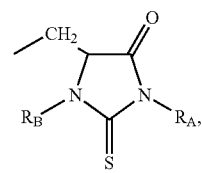

wherein $R_A$ and $R_B$ are independently selected from the group of H and hydrocarbyl;

(b)

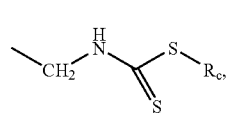

wherein $R_C$ is selected from the group of H and hydrocarbyl;

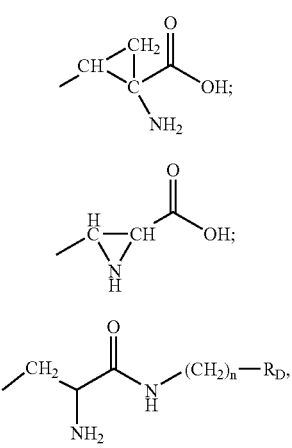

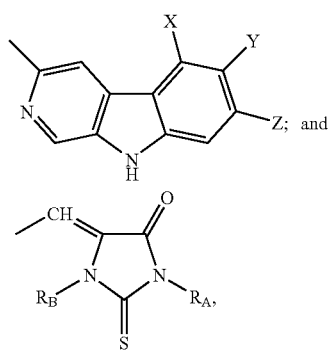

wherein n is a whole number from 1 to 10 and $R_D$ is a carboline substituent of the formula:

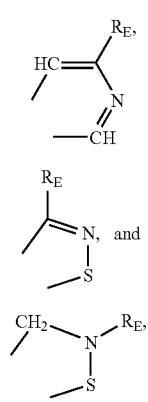

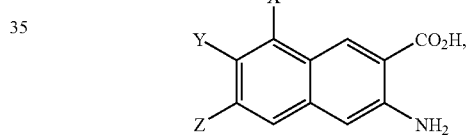

wherein $R_A$ and $R_B$ are independently selected from the group of H and hydrocarbyl; or $R_2$ and $R_3$ are joined together and represent part of a ring which is fused to the pyrrole moiety of formula (I) and which is selected from the group of:

(i)

(ii)

(iii)

wherein $R_E$ is a hydrocarbyl or alkyl-Q, Q representing a substituent of the formula:

the compound of formula (I) being a β-carboline derivative when $R_2$ and $R_3$ joined together represent (i), a brassilexin derivative when $R_2$ and $R_3$ joined together represent (ii), and an N-substituted brassilexin derivative when $R_2$ and $R_3$ joined together represent (iii); X, Y, and Z may be the same or different and are selected from the group consisting of H, halogen, $NO_2$, and hydrocarbyl; and when $R_2$ and $R_3$ are joined together and represent part of a ring system, Y may also be isothiocyanate; with the proviso that formula (I) does not include any of the compounds: 3-(N-methyl-thiohydantoin)-indole, 3-(N-phenyl-thiohydantoin)-indole, 3-(N-allyl-thiohydantoin)-indole, 5-methyl-brassinin, brassinin, brassilexin, β-carboline, 3-butyl-β-carboline, 3-butyl-β-carboline, 6-fluoro-3-carbomethoxy-β-carboline, 6-isothiocyanate-3-carbomethoxy-β-carboline, 3-propoxy-β-carboline, 3-carboxy-β-carboline, 3-carbopropoxy-β-carboline, 3-carbo-tert-butoxy-β-carboline; and formula (II):

wherein X, Y, and Z may be the same or different and are selected from the group consisting of H, halogen, $NO_2$, and hydrocarbyl; and with the proviso that formula (II) does not include 3-amino-2-naphthoic acid.

According to another aspect of the present invention, a method for treating cancer in a patient is provided. The method comprises administering an effective amount of a pharmaceutical composition comprising at least one indoleamine 2,3-dioxygenase (IDO) inhibitor, preferably a novel inhibitor of the instant invention, in a pharmaceutically acceptable carrier medium.

In another embodiment of the invention, a method for treating cancer in a patient in need thereof is provided. The method comprises administering to the patient, concurrently or sequentially, an effective amount of at least one indoleamine 2,3-dioxygenase (IDO) inhibitor and at least one signal transduction inhibitor (STI). In a particular embodiment of the invention, the at least one STI is selected from the group consisting of bcr/abl kinase inhibitors, epidermal growth factor (EGF) receptor inhibitors, her-2/neu receptor inhibitors, and farnesyl transferase inhibitors (FTIs). The compounds may be administered in a pharmaceutically acceptable carrier medium.

In still another embodiment of the invention, another method for treating cancer in a patient in need thereof is provided. The method comprises administering to the patient, concurrently or sequentially, an effective amount of at least one indoleamine 2,3-dioxygenase (IDO) inhibitor and at least one chemotherapeutic agent. In a particular embodiment of the invention, the at least one chemotherapeutic agent is selected from the group consisting of paclitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives. The compounds may be administered in a pharmaceutically acceptable carrier medium.

According to yet another aspect of the instant invention, a method is provided for treating cancer in a patient in need thereof by administering to the patient, concurrently or sequentially, an effective amount of at least one immunomodulator other than an IDO inhibitor and an effective amount of at least one cytotoxic chemotherapeutic agent or at least one STI. In a particular embodiment the at least one immunomodulator is selected from the group consisting of CD40L, B7, B7RP1, ant-CD40, anti-CD38, anti-ICOS, 4-IBB ligand, dendritic cell cancer vaccine, IL2, IL12, ELC/CCL19, SLC/CCL21, MCP-1, IL-4, IL-18, TNF, IL-15, MDC, IFNa/b, M-CSF, IL-3, GM-CSF, IL-13, and anti-IL-10. In another particular embodiment, the at least one cytotoxic chemotherapeutic agent is selected from the group consisting of paclitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives.

In yet another embodiment of the present invention, a method is provided for treating a chronic viral infection in a patient in need thereof by administering to the patient, concurrently or sequentially, an effective amount of at least one indoleamine 2,3-dioxygenase (IDO) inhibitor and at least one chemotherapeutic agent. The at least one chemotherapeutic agent may be selected from the group consisting of paclitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives. The active agents may be administered with or without a pharmaceutically acceptable carrier medium. The method of the invention may be used to treat chronic viral infection selected from the group consisting of: hepatitis C virus (HCV), human papilloma virus (HPV), cytomegalovirus (CMV), Epstein-Barr virus (EBV), varicella zoster virus, coxsackie virus, human immunodeficiency virus (HIV).

BRIEF DESCRIPTION OF THE DRAWINGS

FIG. 24 is a graph of the results from an in vitro biochemical assay for screening of IDO inhibitor candidates. Data is provided relative to the amount of kynurenine produced in the absence of inhibitor.

FIGS. 25A and 25B are graphs of the results from the cell-based assay for screening of IDO inhibitor candidates. In FIG. 25A, data is provided relative to the amount of kynurenine produced in the absence of inhibitor. In FIG. 25B, the data is presented in terms of fluorescence, which is indicative of kynurenine production (i.e., IDO activity). Cells were either transfected with an empty expression vector (vector) or an expression vector containing the cDNA of IDO.

FIG. 27 is a chart of certain IDO inhibitors, their structures, and their ability to inhibit IDO and TDO activity at a concentration of 250 µM in a cell-based assay.

FIG. 28 provides graphs demonstrating the toxicity of certain IDO inhibitors of neoplastically transformed breast (top panel) or prostate (bottom panel) cancer cells. Cells were either untreated (Untx) or treated with 100 µM of inhibitor.

DETAILED DESCRIPTION OF THE INVENTION

Figure 1:
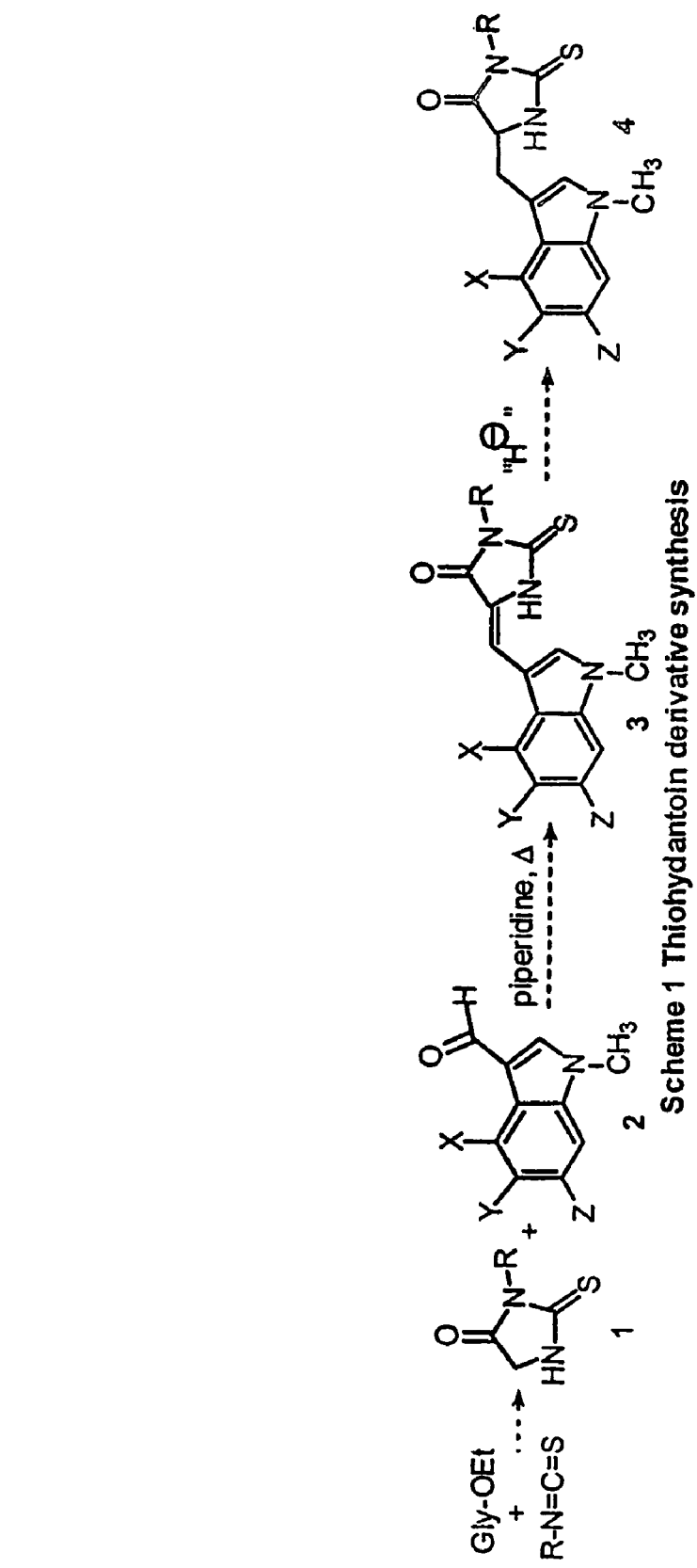
FIG. 1 provides a scheme for synthesizing thiohydantoin derivatives of the present invention.

In one embodiment of the present invention, a group of novel compounds exhibiting IDO inhibitory activity are provided. Also encompassed within the invention are pharmaceutical compositions comprising such compounds and methods of use thereof for inhibiting tumor growth.

In yet another embodiment of the present invention, a combination treatment protocol comprising administration of an IDO inhibitor with a signal transduction inhibitor (STI) is provided, which is effective for suppressing tumor growth.

In accordance with yet another aspect of the present invention, another combination treatment protocol comprising administration of an IDO inhibitor with a chemotherapeutic agent is provided, which is effective for suppressing tumor growth.

In still another embodiment of the present invention, a combination treatment protocol is provided for the treatment of a chronic viral infection, comprising the administration of an IDO inhibitor and a chemotherapeutic agent.

I. Definitions

The term "IDO inhibitor" refers to an agent capable of inhibiting the activity of indoleamine 2,3-dioxygenase (IDO) and thereby reversing IDO-mediated immunosuppression. An IDO inhibitor may be a competitive, noncompetitive, or irreversible IDO inhibitor. "A competitive IDO inhibitor" is a compound that reversibly inhibits IDO enzyme activity at the catalytic site (for example, without limitation, 1-methyl-tryptophan); "a noncompetitive IDO Inhibitor" is a compound that reversibly inhibits IDO enzyme activity at a non-catalytic site (for example, without limitation, norharman); and "an irreversible IDO inhibitor" is a compound that irreversibly destroys IDO enzyme activity by forming a covalent bond with the enzyme (for example, without limitation, cyclopropyl/aziridinyl tryptophan derivatives).

IDO inhibitors of the instant invention may include, without limitation, i) previously established (known) IDO inhibitors, such as, but not limited to: 1-methyl-DL-tryptophan (1 MT; Sigma-Aldrich; St. Louis, Mo.), β-(3-benzofuranyl)-DL-alanine (Sigma-Aldrich), beta-(3-benzo(b)thienyl)-DL-alanine (Sigma-Aldrich), 6-nitro-L-tryptophan (Sigma-Aldrich), indole 3-carbinol (LKT Laboratories; St. Paul, Minn.), 3,3'-diindolylmethane (LKT Laboratories), epigallocatechin gallate (LKT Laboratories), 5-Br-4-Cl-indoxyl 1,3-diacetate (Sigma-Aldrich), 9-vinylcarbazole (Sigma-Aldrich), acemetacin (Sigma-Aldrich), 5-bromo-DL-tryptophan (Sigma-Aldrich), and 5-bromoindoxyl diacetate (Sigma-Aldrich); and ii) the novel IDO inhibitors of the instant invention. In a preferred embodiment of the invention, the IDO inhibitors include the novel IDO inhibitors of the present invention.

A "signal transduction inhibitor" is an agent that selectively inhibits one or more vital steps in signaling pathways, in the normal function of cancer cells, thereby leading to apoptosis.

Signal transduction inhibitors (STIs) of the instant invention include, but are not limited to, (i) bcr/abl kinase inhibitors such as, for example, STI 571 (Gleevec); (ii) epidermal growth factor (EGF) receptor inhibitors such as, for example, kinase inhibitors (Iressa, SSI-774) and antibodies (Imclone: C225 [Goldstein et al. (1995), Clin Cancer Res. 1:1311-1318], and Abgenix: ABX-EGF); (iii) her-2/neu receptor inhibitors such as, for example, Herceptin™ (trastuzumab), and farnesyl transferase inhibitors (FTI) such as, for example, L-744,832 (Kohl et al. (1995), Nat Med. 1(8):792-797); (iv) inhibitors of Akt family kinases or the Akt pathway, such as, for example, rapamycin (see, for example, Sekulic et al. (2000) Cancer Res. 60:3504-3513); (v) cell cycle kinase inhibitors such as, for example, flavopiridol and UCN-01 (see, for example, Sausville (2003) Curr. Med. Chem. Anti-Canc Agents 3:47-56); and (vi) phosphatidyl inositol kinase inhibitors such as, for example, LY294002 (see, for example, Vlahos et al. (1994) J. Biol. Chem. 269:5241-5248).

A "therapeutically effective amount" of a compound or a pharmaceutical composition refers to an amount sufficient to modulate tumor growth or metastasis in an animal, especially a human, including without limitation decreasing tumor growth or size or preventing formation of tumor growth in an animal lacking any tumor formation prior to administration, i.e., prophylactic administration.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, excipient, auxilliary agent or vehicle with which an active agent of the present invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Concurrently" means (1) simultaneously in time, or (2) at different times during the course of a common treatment schedule.

"Sequentially" refers to the administration of one component of the method followed by administration of the other component. After administration of one component, the next component can be administered substantially immediately after the first component, or the next component can be administered after an effective time period after the first component; the effective time period is the amount of time given for realization of maximum benefit from the administration of the first component.

"Hydrocarbyl" refers to an unsubstituted or substituted hydrocarbon moiety containing from about 1 to about 10 carbon atoms or from about 1 to about 25 carbon atoms, which may be a straight, branched, or cyclic hydrocarbon group. When substituted, hydrocarbyl groups may be substituted at any available point of attachment. Exemplary unsubstituted groups include alkyls such as methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, octadecyl, nonadecyl, eicosyl, heneicosyl, docosyl, tricosyl, tetracosyl, pentacosyl, and the like; aryls such as phenyl, tolyl, xylyl, napthyl, biphenyl, tetraphenyl, and the like; aralkyls such as benzyl, phenethyl, phenpropyl, phenbutyl, phenhexyl, napthoctyl, and the like; and cycloalkyls such as cyclopropyl, cyclobutyl, cyclohexyl, cycloheptyl, cyclooctyl, and the like. Exemplary substituents may include but are not limited to one or more of the following groups: halo (such as F, Cl, Br, I), haloalkyl (such as $CCl_3$ or $CF_3$), alkoxy, alkylthio, hydroxy, carboxy (—COOH), carbonyl (—C(=O)), epoxy, alkyloxycarbonyl (—C(=O)—OR), alkylcarbonyloxy (—OC(=O)—R), amino (—$NH_2$), carbamoyl ($NH_2C$(=O)— or NHRC (=O)—), urea (—NH-$CONH_2$), alkylurea (—NHCONHR) or thiol (—SH), wherein R in the aforementioned substituents represents a hydrocarbyl moiety. Hydrocarbyl groups (moieties) as defined herein may also comprise one or more carbon to carbon double bonds or one or more carbon to carbon triple bonds (i.e., the hydrocarbyl groups may be unsaturated). Exemplary unsaturated hydrocarbyl groups include alkenyls such as allyl and vinyl. Hydrocarbyl groups may also be interrupted with at least one oxygen, nitrogen, or sulfur atom.

The terms "halogen," "halo," and "halide" refer to chlorine, bromine, fluorine or iodine.

"Lower alkyl" refers to an alkyl having about 1 to 4 carbon atoms, such as methyl, ethyl, propyl, buytl, and isopropyl. In a certain embodiment, the lower alkyl is methyl.

II. Novel Compounds Exhibiting IDO Inhibitory Activity and Methods of Use

In accordance with the instant invention, novel compounds of the following formulas, which are capable of inhibiting IDO activity and thereby suppressing tumor growth, are provided:

formula (I):

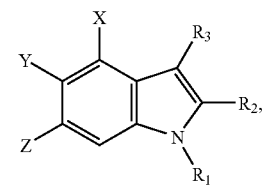

wherein $R_1$ is H or lower alkyl; $R_2$ is H; $R_3$ is selected from the group consisting of: (a)

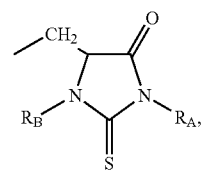

wherein $R_A$ and $R_B$ are independently selected from the group of H and hydrocarbyl; (b)

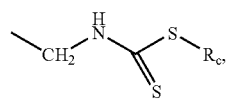

wherein $R_C$ is selected from the group of H and hydrocarbyl;

(c)

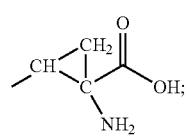

(d)

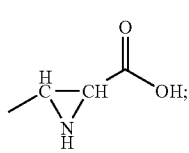

(e)

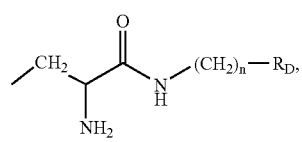

wherein n is a whole number from 1 to 10 and $R_D$ is a carboline substituent of the formula:

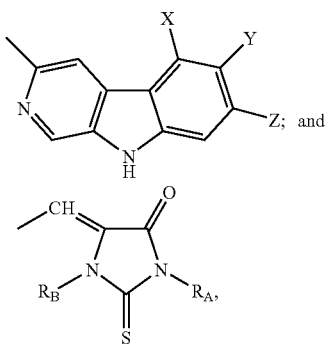

(f)

wherein $R_A$ and $R_B$ are independently selected from the group of H and hydrocarbyl; or $R_2$ and $R_3$ are joined together and represent part of a ring which is fused to the pyrrole moiety of formula (I) and which is selected from the group of:

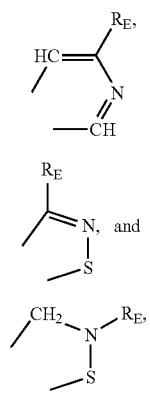

(i)

(ii)

(iii)

wherein $R_E$ is a hydrocarbyl or alkyl-Q, Q representing a substituent of the formula:

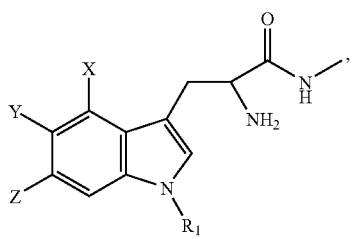

the compound of formula (I) being a β-carboline derivative when $R_2$ and $R_3$ joined together represent (i), a brassilexin derivative when $R_2$ and $R_3$ joined together represent (ii), and an N-substituted brassilexin derivative when $R_2$ and $R_3$ joined together represent (iii); X, Y, and Z may be the same or different and are selected from the group consisting of H, halogen, $NO_2$, and hydrocarbyl; and when $R_2$ and $R_3$ are joined together and represent part of a ring system, Y may also be isothiocyanate; with the proviso that formula (I) does not include a compound selected from the group of: 3-(N-methyl-thiohydantoin)-indole, 3-(N-phenyl-thiohydantoin)-indole, 3-(N-allyl-thiohydantoin)-indole, 5-methyl-brassinin, brassinin, brassilexin, β-carboline, 3-butyl-β-carboline, 6-fluoro-3-carbomethoxy-β-carboline, 6-isothiocyanate-3-carbomethoxy-β-carboline, 3-propoxy-β-carboline, 3-carboxy-β-carboline, 3-carbopropoxy-β-carboline, and 3-carbo-tert-butoxy-β-carboline; and formula (II):

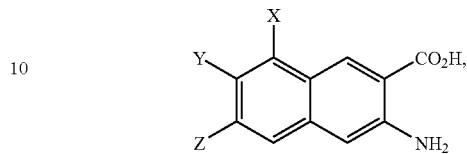

wherein X, Y, and Z may be the same or different and are selected from the group consisting of H, halogen, $NO_2$, and hydrocarbyl; and with the proviso that formula (II) does not include 3-amino-2-naphthoic acid.

In one embodiment of the invention, the novel compounds of formula (I) may be further characterized by the following additional provisos: 1) if $R_3$ is substituent (a) and if $R_A$ is other than H, then either $R_B$ is hydrocarbyl, or at least one of X, Y, or Z is other than H, $NO_2$, COH, $CH_2OH$, or $CH_3$; 2) if $R_3$ is substituent (a) and if $R_B$ is H, then either $R_A$ is H, or at least one of X, Y, or Z is other than H, $NO_2$, COH, $CH_2OH$, or $CH_3$; 3) if $R_3$ is substituent (a) and if X, Y, and Z are all selected from the group consisting of H, $NO_2$, COH, $CH_2OH$, or $CH_3$, then either $R_A$ is H, or $R_B$ is hydrocarbyl.

In yet another embodiment of the invention, the novel compounds of formula (I) may be further characterized by the additional proviso that when $R_3$ is (f), Y is a halogen.

In a particular embodiment of the invention, when $R_3$ is (f), X and Z are H, Y is Br, $R_1$ is —$CH_3$, $R_2$ is H, $R_A$ is —$CH_3$ or —$CH_2$—CH=$CH_2$, and $R_B$ is H.

The compounds of formulas (I) wherein $R_3$ is selected from the group consisting of (a), (b), and (f) and formula (II) are believed to competitively inhibit IDO activity, while the compounds of formulas (I) wherein $R_3$ is selected from the group consisting of (c), (d), and (e) or $R_2$ and $R_3$ are joined to form one of the group consisting of (i), (ii), and (iii) likely inhibit IDO activity noncompetitively.

The present invention also provides pharmaceutical compositions comprising at least one of the IDO inhibitors having a formula selected from formulas (I) and (II) in a pharmaceutically acceptable carrier. Such a pharmaceutical composition may be administered, in a therapeutically effective amount, to a patient in need thereof for the treatment of cancer.

Moreover, the present invention provides a method for the treatment of cancer by administering to a patient, in need thereof, a therapeutically effective amount of at least one IDO inhibitor having the formula selected from formulas (I) and (II).

Cancers that may be treated using the present protocol include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma.

III. Combinatorial Therapies for the Treatment of Cancer

The present invention also provides methods for tumor suppression. In accordance with the present invention, it has been discovered that the combination of an IDO inhibitor with a signal transduction inhibitor (STI) act synergistically to suppress tumor growth. Accordingly, the present invention provides a pharmaceutical composition for the treatment of cancer in a patient comprising at least one IDO inhibitor and at least one STI in a pharmaceutically acceptable carrier. Also provided is a method for treating cancer in a patient by administering an effective amount of at least one IDO inhibitor in combination with at least one STI. Suitable IDO inhibitors include any compound which exhibits IDO inhibitory activity including compounds having a formula selected from formulas (I) and (II). Suitable STIs, as noted hereinabove, include, but are not limited to: (i) bcr/abl kinase inhibitors such as, for example, STI 571 (Gleevec); (ii) epidermal growth factor (EGF) receptor inhibitors such as, for example, kinase inhibitors (Iressa, SSI-774) and antibodies (Imclone: C225 [Goldstein et al. (1995), *Clin Cancer Res.* 1:1311-1318], and Abgenix: ABX-EGF); (iii) her-2/neu receptor inhibitors such as, for example, Herceptin™ (trastuzumab) and farnesyl transferase inhibitors (FTI) such as, for example, L-744,832 (Kohl et al. (1995), *Nat Med.* 1(8):792-797); (iv) inhibitors of Akt family kinases or the Akt pathway, such as, for example, rapamycin (see, for example, Sekulic et al. (2000) Cancer Res. 60:3504-3513); (v) cell cycle kinase inhibitors such as, for example, flavopiridol and UCN-01 (see, for example, Sausville (2003) Curr. Med. Chem. Anti-Canc Agents 3:47-56); and (vi) phosphatidyl inositol kinase inhibitors such as, for example, LY294002 (see, for example, Vlahos et al. (1994) J. Biol. Chem. 269:5241-5248).

In a specific embodiment of the present invention, the at least one IDO inhibitor and at least one STI may be administered to the patient concurrently or sequentially. In other words, the at least one IDO inhibitor may be administered first, the at least one STI may be administered first, or the at least one IDO inhibitor and the at least one STI may be administered at the same time. Additionally, when more than one IDO inhibitor and/or STI is used, the compounds may be administered in any order.

Cancers that may be treated using the present combinatorial protocol include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma.

In addition to IDO, other molecules are known to be involved in immunomodulation. These other molecules may also be potential targets for suppressing tumor growth in cancer patients. Accordingly, the present invention also provides combinatorial methods of treating cancer patients by the administration of at least one immunomodulator other than an IDO inhibitor in conjunction with at least one chemotherapeutic agent. Suitable immunomodulators that may be used in the present invention include, without limitation: costimulatory molecules, such as, CD40L, B7, and B7RP1; activating monoclonal antibodies (mAbs) to costimulatory receptors, such as, ant-CD40, anti-CD38, anti-ICOS, and 4-IBB ligand; dendritic cell antigen loading (in vitro or in vivo); dendritic cell cancer vaccine; cytokines/chemokines, such as, IL1, IL2, IL12, IL18, ELC/CCL19, SLC/CCL21, MCP-1, IL-4, IL-18, TNF, IL-15, MDC, IFNa/b, M-CSF, IL-3, GM-CSF, IL-13, and anti-IL-10; bacterial lipopolysaccharides (LPS); and immune-stimulatory oligonucleotides (e.g., poly CpG DNA (see, for example, Verthelyi and Zeuner (2003) Tr. Immunol. 24:519-522)). Suitable chemotherapeutic agents include, but are not limited to, cytotoxic chemotherapeutic agents and signal transduction inhibitors (STIs).

In accordance with the present invention, it has also been discovered that the combination of an IDO inhibitor with a chemotherapeutic agent act synergistically to suppress tumor growth. Accordingly, the present invention provides a pharmaceutical composition for the treatment of cancer in a patient comprising at least one IDO inhibitor and at least one chemotherapeutic agent in a pharmaceutically acceptable carrier. Also provided is a method for treating cancer in a patient by administering an effective amount of at least one IDO inhibitor in combination with at least one chemotherapeutic agent. Suitable IDO inhibitors include any compound which exhibits IDO inhibitory activity including compounds having a formula selected from formulas (I) and (II). Suitable chemotherapeutic agents, as noted hereinabove, include, but are not limited to: paclitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives.

In a specific embodiment of the present invention, the at least one IDO inhibitor and at least one chemotherapeutic agent may be administered to the patient concurrently or sequentially. In other words, the at least one IDO inhibitor may be administered first, the at least one chemotherapeutic agent may be administered first, or the at least one IDO inhibitor and the at least one chemotherapeutic agent may be administered at the same time. Additionally, when more than one IDO inhibitor and/or chemotherapeutic agent is used, the compounds may be administered in any order.

Cancers that may be treated using the present combinatorial protocol include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma.

IV. Combinatorial Therapy for the Treatment of Chronic Viral Infections

The present invention further provides a pharmaceutical composition for the treatment of a chronic viral infection in a patient comprising at least one IDO inhibitor, at least one cancer therapeutic drug in a pharmaceutically acceptable carrier, and, optionally, at least one antiviral agent. Also provided is a method for treating a chronic viral infection in a patient by administering an effective amount the composition just described.

Suitable IDO inhibitors include any compound which exhibits IDO inhibitory activity including compounds having a formula selected from formulas (I) and (II).

Suitable chemotherapeutic agents are any compounds that exhibit anticancer activity including, but not limited to: alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, vinblastine, and paclitaxel (Taxol)); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). Preferably, the chemotheraputic agent is selected from the group consisting of: paclitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives.

Suitable antiviral agents include, without limitation: acyclovir; gangcyclovir; foscarnet; ribavirin; and antiretrovirals such as, for example, nucleoside analogue reverse transcriptase inhibitors (e.g., azidothymidine (AZT), ddl, ddC, 3TC, d4T), non-nucleoside reverse transcriptase inhibitors (e.g., efavirenz, nevirapine), nucleotide analogue reverse transcriptase inhibitors, and protease inhibitors.

In a specific embodiment of the present invention, the at least one IDO inhibitor and at least one chemotherapeutic agent may be administered to the patient concurrently or sequentially. In other words, the at least one IDO inhibitor may be administered first, the at least one chemotherapeutic agent may be administered first, or the at least one IDO inhibitor and the at least one STI may be administered at the same time. Additionally, when more than one IDO inhibitor and/or chemotherapeutic agent is used, the compounds may be administered in any order. Similarly, the antiviral agent may also be administered at any point.

The compounds of this combination treatment may also be administered for localized infections. Specifically, the at least one IDO inhibitor, at least one chemotherapeutic agent, and, optionally, at least one antiviral agent may be administered to treat skin infections such as shingles and warts. The compounds may be administered in any pharmaceutically acceptable topical carrier including, without limitation: gels, creams, lotions, ointments, powders, aerosols and other conventional forms for applying medication to the skin.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, coxsackie virus, human immunodeficiency virus (HIV).

Notably, parasitic infections (e.g. malaria) may also be treated by the above methods wherein compounds known to treat the parasitic conditions are optionally added in place of the antiviral agents.

V. Administration of Pharmaceutical Compositions and Compounds

The pharmaceutical compositions of the present invention can be administered by any suitable route, for example, by injection, by oral, pulmonary, nasal or other modes of administration. In general, pharmaceutical compositions of the present invention, comprise, among other things, pharmaceutically acceptable diluents, preservatives, solubilizers, emulsifiers, adjuvants and/or carriers. Such compositions can include diluents of various buffer content (e.g., Tris-HCl, acetate, phosphate), pH and ionic strength; and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The compositions can be incorporated into particulate preparations of polymeric compounds such as polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington's Pharmaceutical Sciences, 18th Ed. (1990, Mack Publishing Co., Easton, Pa. 18042) pages 1435-1712 which are herein incorporated by reference. The pharmaceutical composition of the present invention can be prepared, for example, in liquid form, or can be in dried powder form (e.g., lyophilized).

In yet another embodiment, the pharmaceutical compositions of the present invention can be delivered in a controlled release system, such as using an intravenous infusion, an implantable osmotic pump, a transdermal patch, liposomes, or other modes of administration. In a particular embodiment, a pump may be used (see Langer, supra; Sefton, CRC Crit. Ref. Biomed. Eng. (1987) 14:201; Buchwald et al., Surgery (1980) 88:507; Saudek et al., N. Engl. J. Med. (1989) 321: 574). In another embodiment, polymeric materials may be employed (see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. (1983) 23:61; see also Levy et al., Science (1985) 228:190; During et al., Ann. Neurol. (1989) 25:351; Howard et al., J. Neurosurg. (1989) 71:105). In yet another embodiment, a controlled release system can be placed in proximity of the target tissues of the animal, thus requiring only a fraction of the systemic dose (see, e.g., Goodson, in Medical Applications of Controlled Release, supra, (1984) vol. 2, pp. 115-138). In particular, a controlled release device can be introduced into an animal in proximity to the site of inappropriate immune activation or a tumor. Other controlled release systems are discussed in the review by Langer (Science (1990) 249:1527-1533).

The following examples are provided to illustrate various embodiments of the present invention. These examples are not intended to limit the invention in any way.

Example 1

Synthesis of Thiohydantoin Derivatives

Overview: Thiohydantoin derivatives, or compounds of formula (I) wherein $R_3$ is group (a), were identified by screening commercially available tryptophan derivatives. N-Methyl ($R_1$=H; $R_A$=CH$_3$; $R_B$=H; X, Y, Z=H), N-allyl ($R_1$=H; $R_A$=CH$_2$CH=CH$_2$; $R_B$=H; X, Y, Z=H) and N-phenyl ($R_1$=H; $R_A$=Ph; $R_B$=H; X, Y, Z=H) thiohydantoin derivatives demonstrated greater than 50% inhibition and significant selectivity over the structurally distinct enzyme tryptophan 2,3-dioxygenase (TDO2). To further improve inhibitor potency, the focus of the present invention can be on substitution of the indole ring, a procedure which has enhanced potency of tryptophan derivatives in the past. In particular, literature reports indicate that N-1, C-5 and C-6 substitution of the indole ring will afford more potent inhibitors (Cady and Sono (1991) Arch. Biochem. Biophys., 291:326-33; Munn, D. H., et al. (1998) Science, 281:1191-3; Peterson, A. C., et al. (1994) Med. Chem. Res., 3:531-544; Southan, M. D., et al. (1996) Med. Chem. Res., 6: 343-352). Additionally, while C-4 halide derivatives have not been reported in the literature (Southan et al.), the instant invention has identified 5-bromo-4-chloroindoxyl 1,3-diacetate as a potent inhibitor (greater than 50% inhibition of IDO at 250 μM).

Synthesis: Thiohydantoin derivatives can be synthesized via an Erlenmeyer-Plochl azlactone-type condensation reaction between an indole-3-carboxaldehyde and thiohydantoin 1 (FIG. 1; Djura and Faulkner (1980) J. Org. Chem., 45:735-7; Guella, G., et al. (1988) Helv. Chim. Acta, 71:773-82; Guella, G., et al. (1989) Helv. Chim. Acta, 72:1444-50; Crawford and Little (1959) J. Chem. Soc., 729-731; Julian and Sturgis (1935) J. Am. Chem. Soc., 1126-28). A mixture of conjugated alkene stereoisomers 3 will likely result and these products can be tested as planar analogues of the thiohydantoins. Reduction of the conjugated alkene in 3 can be performed by nucleophilic reductants (e.g. NaBH$_4$, Li(s-Bu)$_3$BH, and [(Ph$_3$P)CuH]$_6$) as the presence of sulfur will prohibit more commonly used catalytic hydrogenation methods.

The thiohydantoins can be synthesized by the reaction of, for example, glycine methyl ester or glycine ethyl ester with alkyl isothiocyanates (FIG. 1; Sim and Ganesan (1997) J. Org. Chem., 62:3230-35). Notably, this method of thiohydantoin synthesis allows for a variety of alkyl groups to be incorporated at the N-1 nitrogen atom via reductive amination (Sim and Ganesan (1997) J. Org. Chem., 62:3230-35) and N-3 nitrogen atom depending on the choice of isothiocyanate reagent.

Figure 2:
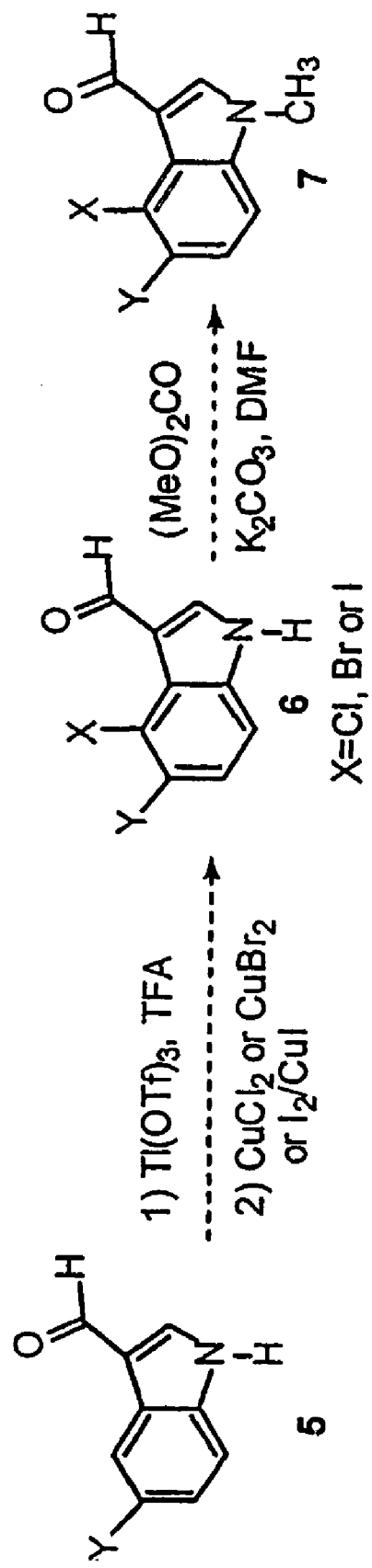
FIG. 2 provides a scheme of the present invention for derivatizing indole at C-4 and N-1 positions.

Based on previous IDO inhibitor studies, a variety of halo-substituted indole-3-carboxaldehydes can be used in the condensation reactions with thiohydantoins. 5-Bromo- and 5-chloroindole-3-carboxaldehyde are commercially available. Substitution in the C-4 position of the indole-3-carboxaldehyde can be accomplished by thallation-halogenation of indole-3-carboxaldehydes 5 (FIG. 2; Somei, M., et al. (1984) Heterocycles, 22(4):797-801; Ohta, T., et al. (1987) Heterocycles 26:2817-22; Somei, M., et al. (1985) Chem. Pharm. Bull. 33:3696-708). N-methylation of the indole-3-carboxaldehydes 6 can be performed by reacting with a dimethyl carbonate (Jiang, X., et al. (2001) Org. Proc. Res. Dev., 5:604-8).

Figure 3:
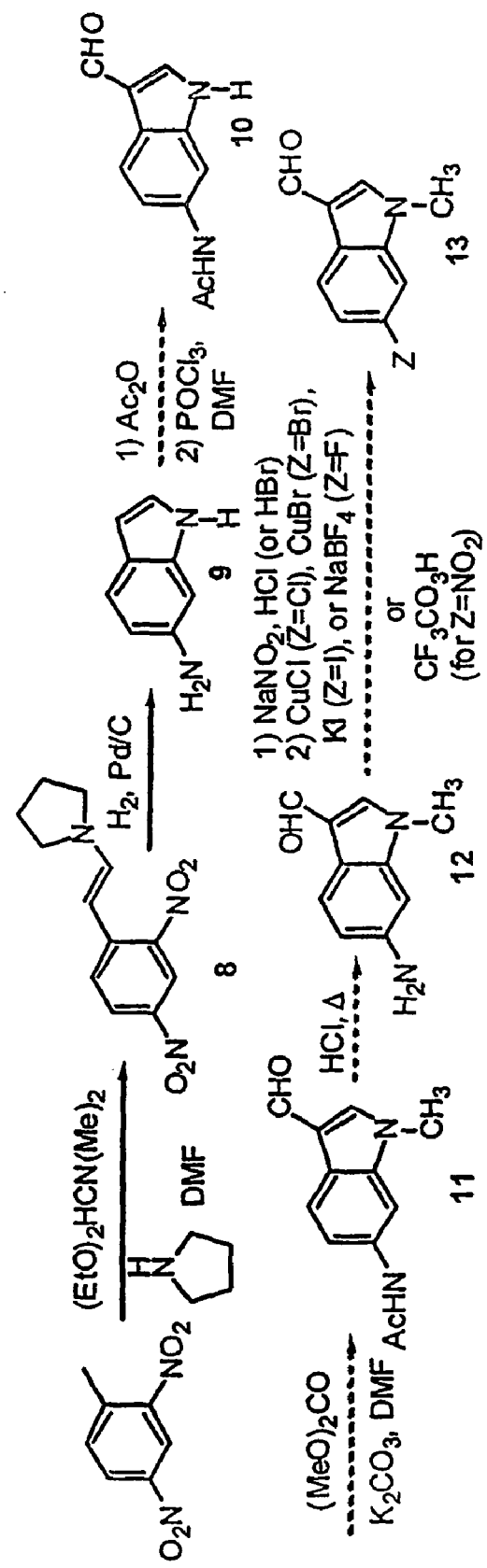
FIG. 3 provides a scheme for synthesizing C-6 substituted indoles of the present invention.

Generation of 6-halo-indole-3-carboxaldehydes can proceed via 6-aminoindole, which is readily synthesized from commercially available 2,4-dinitrotoluene via a Leimgruber-Batcho indole synthesis (FIG. 3; Batcho and Leimgruber (1990) Org. Syn. Coll., 3:34). The 6-amino group can be protected as an acetamide. Vilsmeier formylation of the C-3 position can provide the 6-substituted indole-3-carboxaldehyde 10 (Smith, G. F. (1954) J. Chem. Soc., 3842-6; James and Snyder (1963) Org. Syn. Coll., 4:539). The presence of an electron-releasing acetamide group can enhance the efficiency of the Vilsmeter formylation. Methylation of the indole nitrogen can proceed as described previously. The 6-amino group can be deprotected under acid reflux conditions and then the amine 12 can be transformed into a halogen via Sandmeyer or Schiemann reaction (Somei, M., et al. (1985) Chem. Pharm. Bull., 33:3696-708; Somei and Tsuchiya (1981) Chem. Pharm. Bull., 29:3145-57; Moriya, T., et al. (1975) Bull. Chem. Soc. Jpn., 48:2217-8) or oxidized to a nitro group with a peroxyacid (Pagano and Emmons, Org. Syn. Coll., 5:367). Problems with side reactions involving the 3-carboxaldehyde during the Sandmeyer, Schiemann or amine oxidation reactions can be overcome by altering the sequence to introduce the 3-carboxaldehyde and methylate at the N-1 position later.

Figure 4:
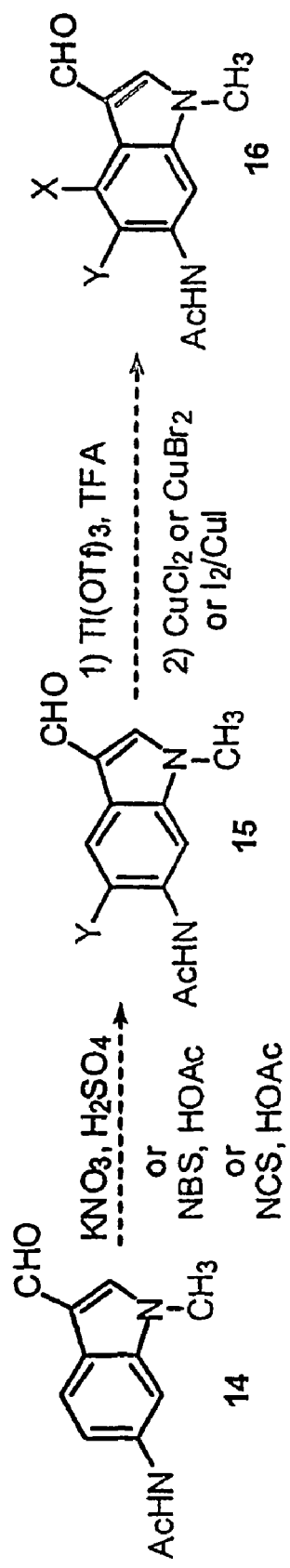
FIG. 4 provides a scheme for synthesizing C-4, C-5, and C-6 trisubstituted indoles of the present invention.

Derivatives with substitution at both the 5 and 6 positions can be synthesized via electrophilic aromatic substitution of 14 (FIG. 4). Nitration of 1-methyl-indole-3-carboxaldehyde has reportedly afforded a 93% yield of a mixture of the 5-nitro and 6-nitro products (Da Settimo and Saettone (1965) Tetrahedron 21:1923-9). Use of the 6-acetamido derivative prevents nitration at the 6 position and further activates the 5 position to eletrophilic aromatic substitution. In addition to nitration, bromination and chlorination may also be employed and thereby allow a variety of 5,6-disubstituted indole-3-carboxaldehydes to be synthesized. In addition, thallation-halogenation (Somei, M., et al. (1984) Heterocycles, 22(4):797-801; Ohta, T., et al. (1987) Heterocycles, 26:2817-22; Somei, M., et al. (1985) Chem. Pharm. Bull., 33:3696-708) of the 5,6-disubstituted indole-3-carboxaldehydes 15 permits functionalization of the C-4 position. Furthermore, following the methods elaborated in Scheme 3 (FIG. 3), the C-4 acetamide group can be modified. When combined, these procedures allow complex polysubstituted indole-3-carboxaldehydes to be obtained in a highly efficient manner.

Notably, IDO demonstrates a preference for L-tryptophan (Peterson, A. C., et al. (1994) Med. Chem. Res., 3:531-544), but will also accept D-tryptophan as a substrate (Sono, M. (1989) Biochemistry, 28:5400-7). Therefore, an enantiomerically pure product may not be absolutely required.

Figure 5:
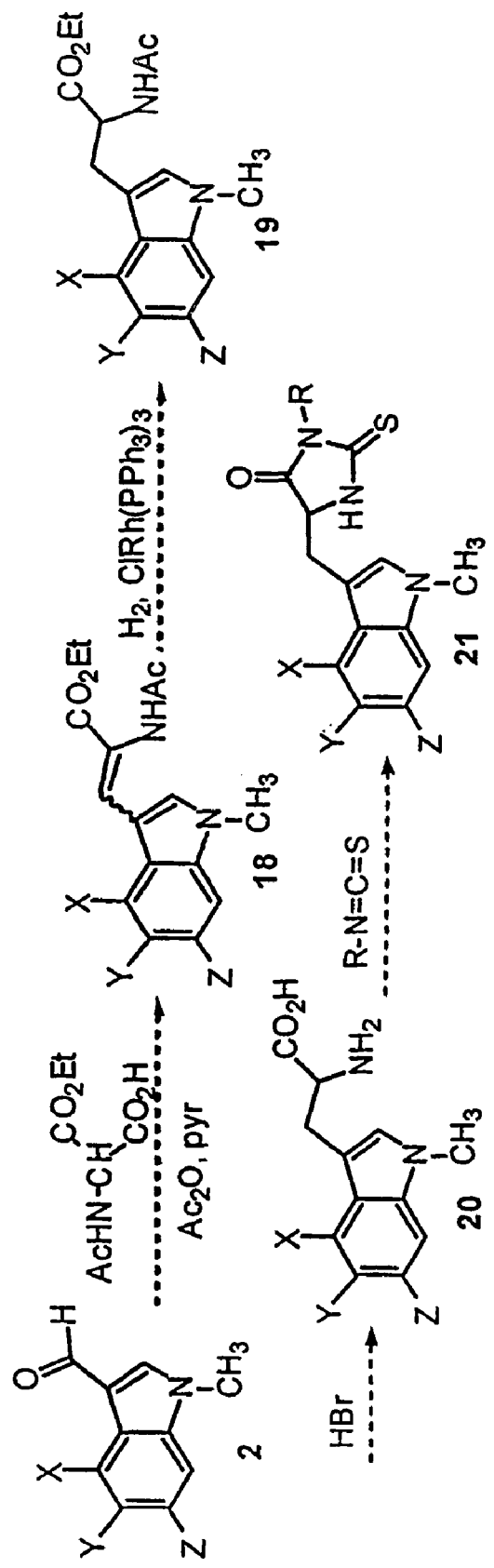
FIG. 5 provides an alternative synthesis scheme of thiohydantoin derivatives of the present invention.

An alternative approach for the synthesis of thiohydantoin derivatives involves the condensation of 2 with the ethyl half ester of acetamidomalonic acid (FIG. 5; Hengartner, U., et al. (1979) J. Org. Chem., 44:3741-7). Hydrogenation with Wilkinson's catalyst generates 19 (Horwell, D. C., et al. (1994) J. Org. Chem., 59:4418-23). Hydrolysis of the acetamide and ethyl ester affords the tryptophan analogue 20. Reaction with alkyl isothiocyanate affords the thiohydantoin product (Cejpek, K., et al. (2000) J. Agric. Food. Chem., 48:3560-5; Mizrach and Polonska (1987) Khim. Farm. Zh., 21:322-8), although it may be more efficient to perform the isothiocyanate reaction on the analogous amino ester (Sim and Ganesan (1997) J. Org. Chem., 62:3230-35).

A potentially important benefit of the alternative path is the ability to obtain an enantiomeriaclly enriched product. Several asymmetric hydrogenations of related dehydrotryptopha compounds have been reported (Hengartner, U., et al. (1979)

J. Org. Chem., 44:3741-7; Knowles, W. S., et al. (1975) J. Am. Chem. Soc., 97:2567-8). Therefore, substitution of the triphenylphophine ligands of Wilkinson's catalyst with chiral phosphine ligands can result in stereoselective synthesis of the L isomer of the tryptophan analogue.

Example 2

Synthesis of Brassinin Derivatives

Overview: Brassinin and related phytoalexins have demonstrated anticancer properties, reportedly due to preventative effects achieved by carcinogen detoxification (Park and Pezzuto (2002) Cancer Metathesis Rev., 21:231-255; Mehta, R. G., et al. (1995) Carcinogenesis 16:399-404; Mehta, R. G., et al. (1994) Anticancer Research 14:1209-1213). Interestingly, brassilexin, a related phytoalexin, is reportedly a non-competitive inhibitor of IDO (Peterson, A. C., et al. (1993) Med. Chem. Res., 3:473-482), whereas, preliminary work indicates brassinin is a competitive inhibitor of IDO. To date, there have been no studies of IDO inhibition with brassinin derivatives (i.e. compounds having the formula of formula (I) wherein $R_3$ is group (b) or brassilexin derivatives (i.e., compounds having the formula of formula (I) wherein $R_3$ and $R_2$ are joined to form (ii) or (iii)). The structural similarity of brassinin to tryptophan and its identification as a competitive inhibitor suggest derivatization similar to tryptophan-based inhibitors already reported.

Figure 6:
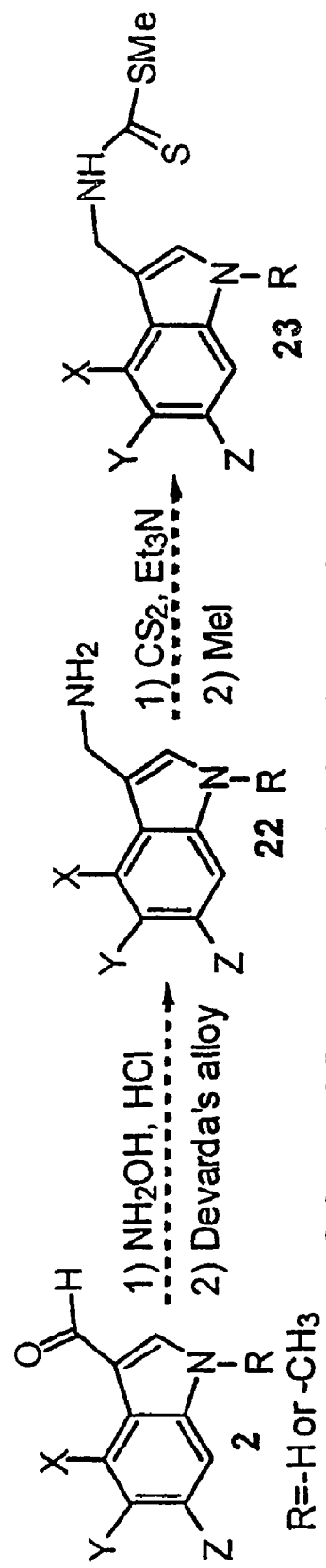
FIG. 6 provides a scheme for synthesizing brassinin derivatives of the present invention.

Synthesis: Indole-3-carboxaldehydes discussed above (FIGS. 2-4) can be employed to generate brassinin derivatives, i.e., IDO inhibitors having the formula of formula (I) where $R_3$ is group (b). The indole-3-carboxaldehydes 2 can be transformed into 3-aminomethyl derivatives 22 by reductive amination with hydroxylamine (FIG. 6). The 3-aminomethylindole derivatives may be unstable (Kutschy, P., et al. (1991) Synlett, 289-290; Kutschy, P., et al. (1998) Tet. 54:3549-66) and therefore will immediately be treated with carbon disulfide and then methyl iodide to generate brassinin derivatives with substitution in the benzene ring (Takasugi, M., et al. (1988) Bull. Chem. Soc. Jpn. 61:285; Pedras, M. S. C., et al. (1992) Life Science Advances (Phytochemistry), 11:1; Mehta, R. G., et al. (1995) Carcinogenesis, 16(2):399-404).

Example 3

Synthesis of β-Carboline Derivatives

Overview: β-Carboline or norharman derivatives, i.e., compounds having the structure of formula (I) wherein $R_3$ and $R_2$ are joined to form (i), have been previously reported (Sono and Cady (1989) Biochemistry, 28:5392-5399; Peterson, A. C., et al. (1993) Med. Chem. Res., 3:473-482; Eguchi, N., et al. (1984) Arch. Biochem. Biophys., 232(2):602-609). However, analogues of the most active derivative, 3-butyl-β-carboline, have not been reported. Notably, substitution at the C-6 position (—F and —N═C═S) of the β-carboline core yielded several similarly active derivatives, but analogues that combine the C-3 and C-6 substitution were not tested; nor were any other substitutions larger than the C-3 butyl of the β-carboline explored (Peterson, A. C., et al. (1993) Med. Chem. Res. 3:473-482). β-carboline derivatives with substitution at the C-5, 7, and 8 position have also not been reported. Of particular interest is the reported mechanism of action of β-carboline derivatives as non-competitive inhibitors, e.g., competition with oxygen for a binding site on the heme iron of the ferrous enzyme (Sono and Cady (1989) Biochemistry, 28:5392-5399).

Figure 7:
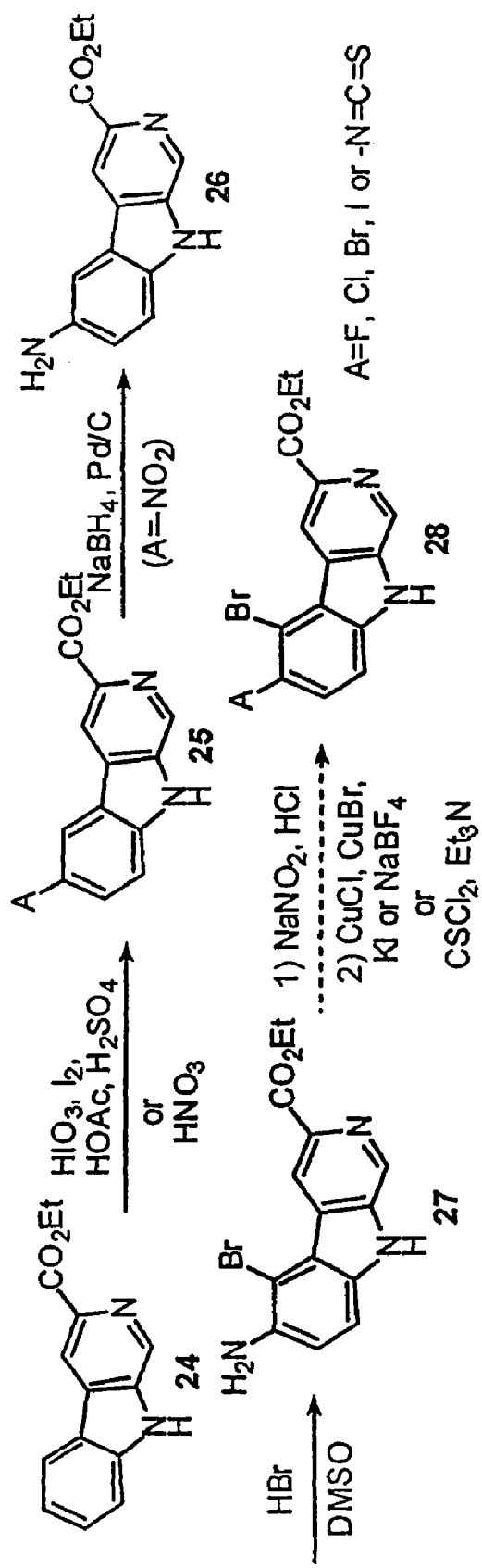
FIG. 7 provides a scheme for synthesizing C-5 and C-6 substituted β-carboline derivatives of the present invention.

Synthetic: The commercially availability of ethyl β-carboline-3-carboxylate 24 makes chemical modifications of this structure attractive for the synthesis of β-carboline derivatives (FIG. 7). Nitration (Settimj, G., et al. (1988) J. Heterocyclic Chem. 25:1391-7) and iodination (Huth, A., et al. (1987) Tet. 43:1071-4) of the C-6 position of 24 has been accomplished in good yield. In addition, regioselective bromination (Ponce and Erra-Balsells (2001) J. Heterocyclic Chem. 38:1087-1095; Kardono, L. B. S., et al. (1991) J. Nat. Prod. 54:1360-7) and chlorination (Ponce, M. A., et al. (2003) J. Heterocyclic Chem. 40:419-426) procedures for β-carboline have also been reported. Reduction of the C-6 nitration product has been accomplished (Settimj, G., et al. (1988) J. Heterocyclic Chem. 25:1391-7) and the resulting amine has been used to direct bromination in the C-5 position of the β-carboline (Huth, A., et al. (1987) Tet. 43:1071-4). These reactions will facilitate the synthesis of C-5 and C-6 substituted β-carboline derivatives.

Figure 8:
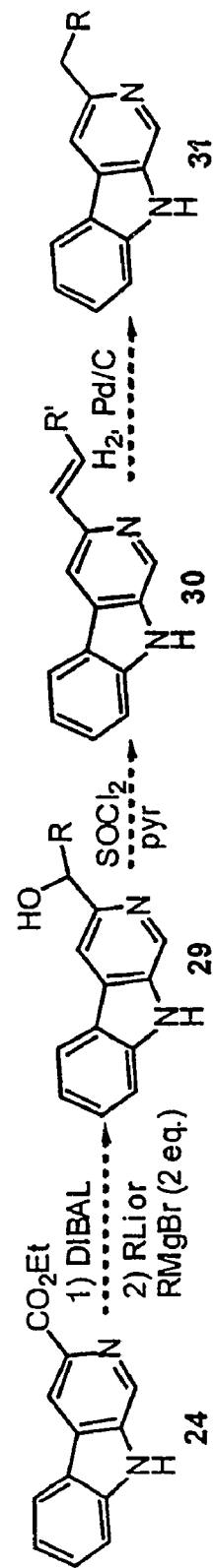
FIG. 8 provides a scheme for synthesizing C-3 alkyl substituted β-carboline derivatives of the present invention.

Derivatization of the C-3 position may be performed via the C-3 carboxaldehyde (FIG. 8). Chemoselective reduction (or reduction to the alcohol and chemoselective oxidation) of the C-3 ester of 24 with DIBAL affords the C-3 carboxaldehyde. Addition of organolithium or Grignard reagents to the aldehyde affords alcohol derivatives 29. Dehydration of the alcohol affords an alkene 30 that can be selectively reduced to yield the C-3 alkyl group of variable length depending on the choice of organometallic reagent. The alcohol and alkene intermediates may also be tested. Alternatively, Wittig reaction with the carboxaldehyde can produce the alkene.

Figure 9:
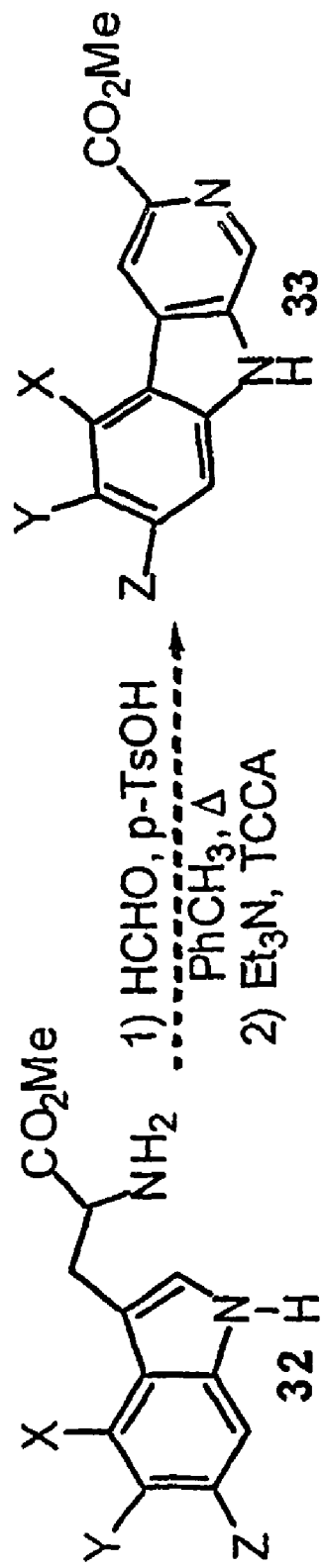
FIG. 9 provides an alternative synthesis scheme of β-carboline derivatives of the present invention.

An alternative approach to β-carboline derivatives involves cyclization and oxidation of tryptophan derivatives 32 (FIG. 9; Haffer, G., et al. (1998) Heterocycles 48(5):993-8). The tryptophan derivatives discussed earlier (FIGS. 2-4) are amenable to cyclization to form the pyrido-indole structure. One advantage in using this procedure is the ability to create potential β-carboline based IDO inhibitors with functionalization in the C-7 position of β-carboline.

Example 4

Synthesis of 3-Amino-2-Naphthoic Acid Derivatives

Overview: In 1994, Peterson and co-workers reported 3-amino-2-naphthoic acid to be the most potent IDO inhibitor amongst a selection of tryptophan derivatives and related compounds (Peterson, A. C., et al. (1994) Med. Chem. Res. 3:531-544). Notably, there were no other derivatives of 3-amino-2-napthoic acid reported in the article, nor, insofar as is known, have other tests with this structure of related derivatives been reported, despite the fact that the compound was more potent than the prototypical IDO inhibitor L-1-methyl-tryptophan (1MT). Since 3-amino-naphthoic acid is a competitive inhibitor, derivatives with substituents in the C-6, C-7, and C-8 positions of the naphthalene core (analogous to the C-4, C-5, and C-6 positions of the indole ring in tryptophan) can provide a superior IDO inhibitor.

Figure 10:
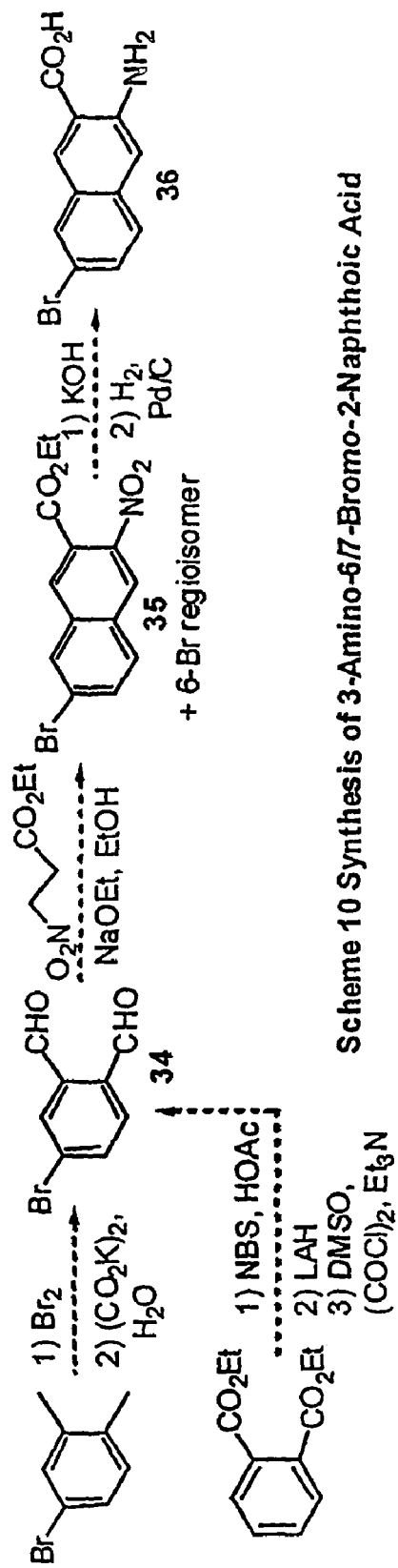
FIG. 10 provides a scheme for synthesizing 3-amino-6/7-bromo-2-naphthoic acid of the present invention.

Synthesis: Although there exist many methods to synthesize naphthalene compounds (de Koning, C. B., et al. (2003) Tet. 59:7-36), the synthesis of asymmetrically substituted naphthalenes with substituents in both rings remains a challenge. However, substituted 3-amino-2-naphthoic acids can be generated by first performing a benzannulation of substituted phthaldehydes (Kienzle, F. (1980) Helv. Chim. Acta 63:2364-9; Singh and Khade (2002) Bioconj. Chem. 13:1286-91). The rapid synthsis of 3-amino-7-bromo-2-naphthoic acid 36 demonstrates the efficiency of this methodology (FIG. 10).

The phthaldehyde 34 can be synthesized from 4-bromo-o-xylene or dimethyl phthalate. Ethyl 3-nitropropionate can be synthesized in one step from silver nitrite and ethyl 3-bromopropionate (Belikov, V. M. (1956) Izv. Akad. Nauk., S. S. S. R.; Otdel. Khim. Nauk 855-62; Chemical abstract (1957) 51:1837j). Condensation of the two affords a mixture of 6-bromo and 7-bromo 3-nitro-2-naphthoic acids 35. Reduction of the nitro group and hydrolysis of the ester affords the brominated 3-amino-2-naphthoic acids. The two regioisomers may be separated at some point in the synthesis, but both compounds can also be tested and the rapid manner in which the two are assembled likely outweighs any inconveniences of the regioisomeric mixture.

Figure 11:
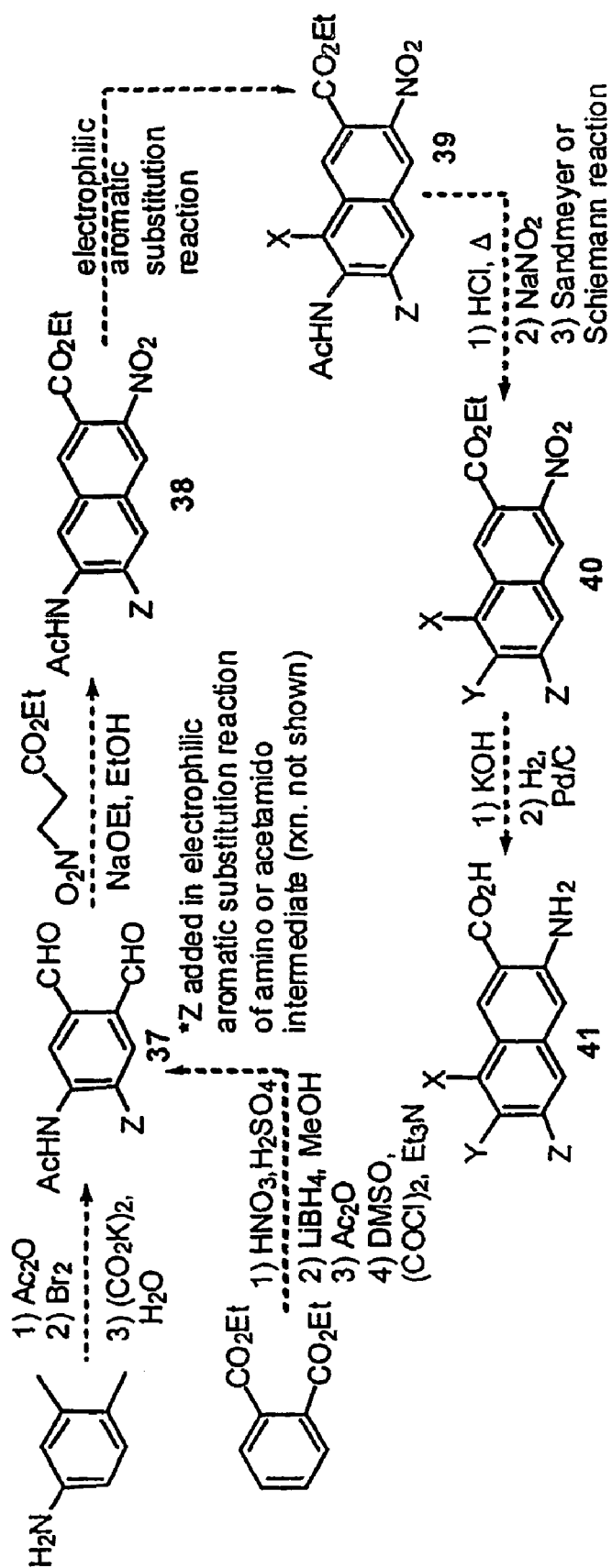
FIG. 11 provides a scheme for synthesizing C-6, C7, and C-8 trisubstituted 3-amino-2-naphthoic acids of the present invention.

The synthesis of additional substituted 3-amino-2-naphthoic acids allows for regiocontrol through the use of electron donating groups in place of the bromine (FIG. 11). The phthaldehydes 37 can be generated from either 3,4-dimethylaniline or dimethyl phthalate. Electrophilic aromatic substitution of the amino or acetamido phthaldehyde precursors allows for the incorporation of groups in the C-6 position of the 3-amino-2-naphthoic acid. The benzannulation reaction is regioselective due to electron releasing acetamido group (Kienzle, F. (1980) Helv. Chim. Acta 63:2364-9). After benzannulation, the 7-acetamido or amino group allows for the efficient substitution at C-8 via electrophilic aromatic substitution reactions. Upon deprotection, the 7-amino group can undergo diazotization and Sandmeyer or Schiemann reaction to afford a variety of substituents. Nitro group reduction and ester hydrolysis affords the 3-amino-2-naphthoic acid derivatives, i.e. compounds of formula (II) for testing.

Figure 12:
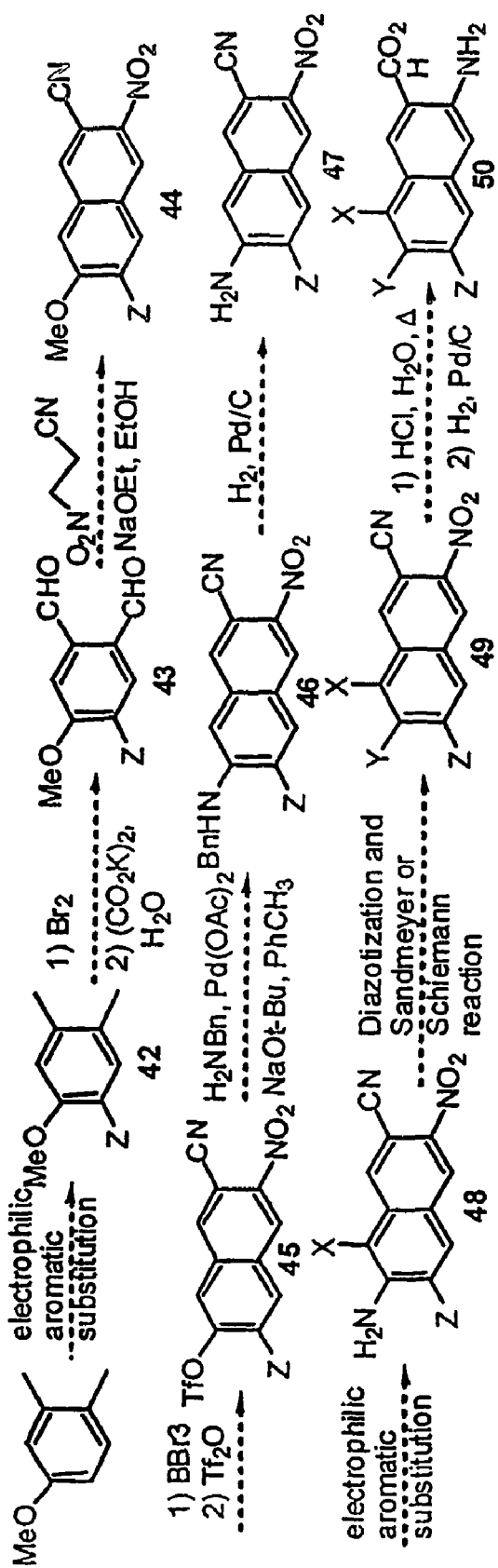
FIG. 12 provides an alternative synthesis scheme of C-6, C-7, and C-8 trisubstituted 3-amino-2-naphthoic acids of the present invention.

As an alternative method, methoxy phthaldehydes 43 (Z=H) have demonstrated considerable control in condensation reactions with 3-nitropropionates (FIG. 12; Kienzle, F. (1980) Helv. Chim. Acta 63:2364-9). The methoxy group directs electrophilic aromatic substitution reactions to ortho positions, however to transform the methoxy group into an amine and subsequently to a halogen, one can employ the Buchwald-Hartwig amination methodology (Wolfe, J. P., et al. (2000) J. Org. Chem. 65:1158-74; Wolfe and Buchwald (1997) J. Org. Chem. 62:1264-7; Louie, J., et al. (1997) J. Org. Chem. 62:1268-73; Hartwig, J. F. (1998) Angew. Chem. Int. Ed. Engl. 37:2046-67). Conversion of the methoxy to triflate 45 allows for amination, but carboxylic esters are not compatible with this process due to the strongly basic conditions. Consequently, 3-nitro-propanenitrile, which can be synthesized similarly to ethyl 3-nitropropionate but with 3-bromopropionitrile as starting material, can be used in the condensation and the cyano group can be hydrolyzed at the end of the synthsis.

Example 5

Synthesis of Brassilexin Derivatives

Figure 13:
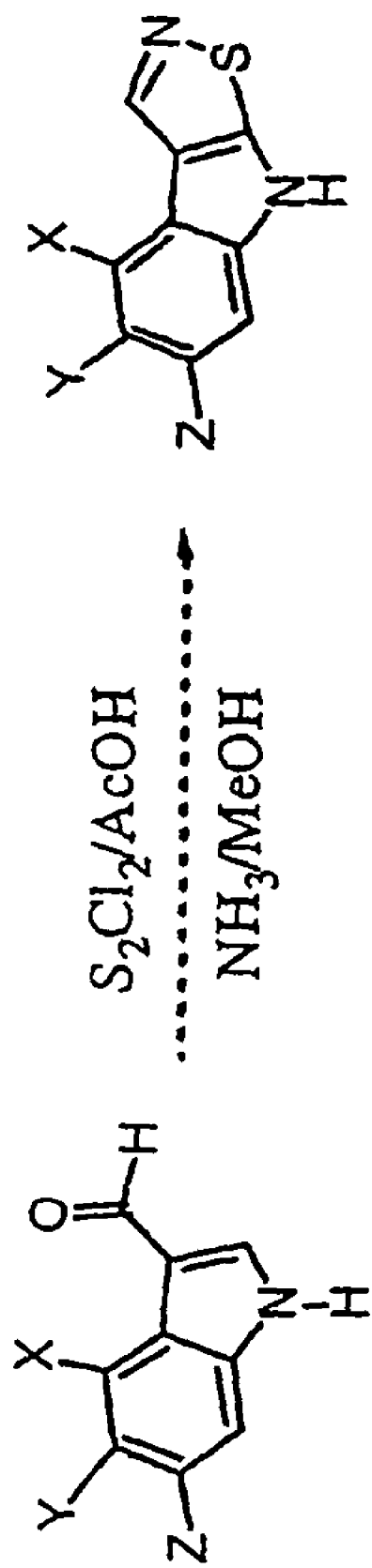
FIG. 13 provides a scheme for synthesizing brassilexin derivatives of the present invention.

Brassilexin derivatives, compounds of formula (I), wherein $R_3$ and $R_2$ are joined to form (ii) or (iii) can be synthesized as shown in FIG. 13 (see, for example, Devys and Barbier (1993) Org. Prep. Proc. Int. 25:344-346).

Figure 14:
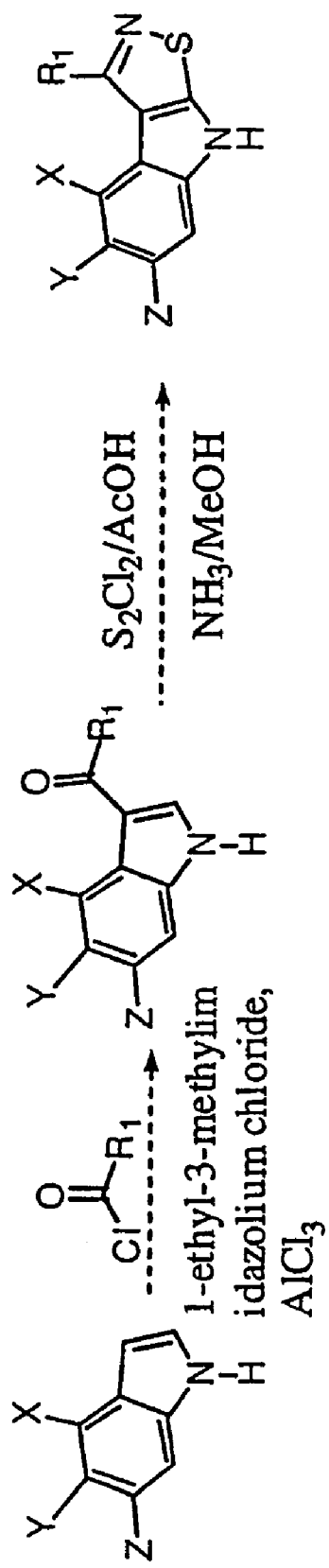
FIG. 14 provides an alternative scheme for synthesizing substituted brassilexin derivatives of the present invention.
Figure 15:
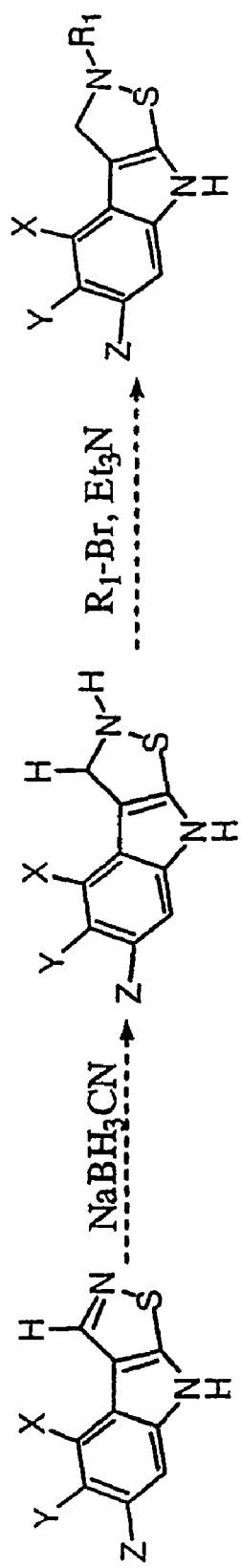
FIG. 15 provides a scheme for synthesizing N-substituted brassilexin derivatives of the present invention.

The synthesis scheme for substituted brasilexin derivatives is shown in FIGS. 14 and 15 (see, for example, Yeung et al. (2002) Tet. Lett. 43:5793-5795).

Example 6

Synthesis of Cyclopropyl/Aziridinyl Tryptophan Derivatives

Figure 16:
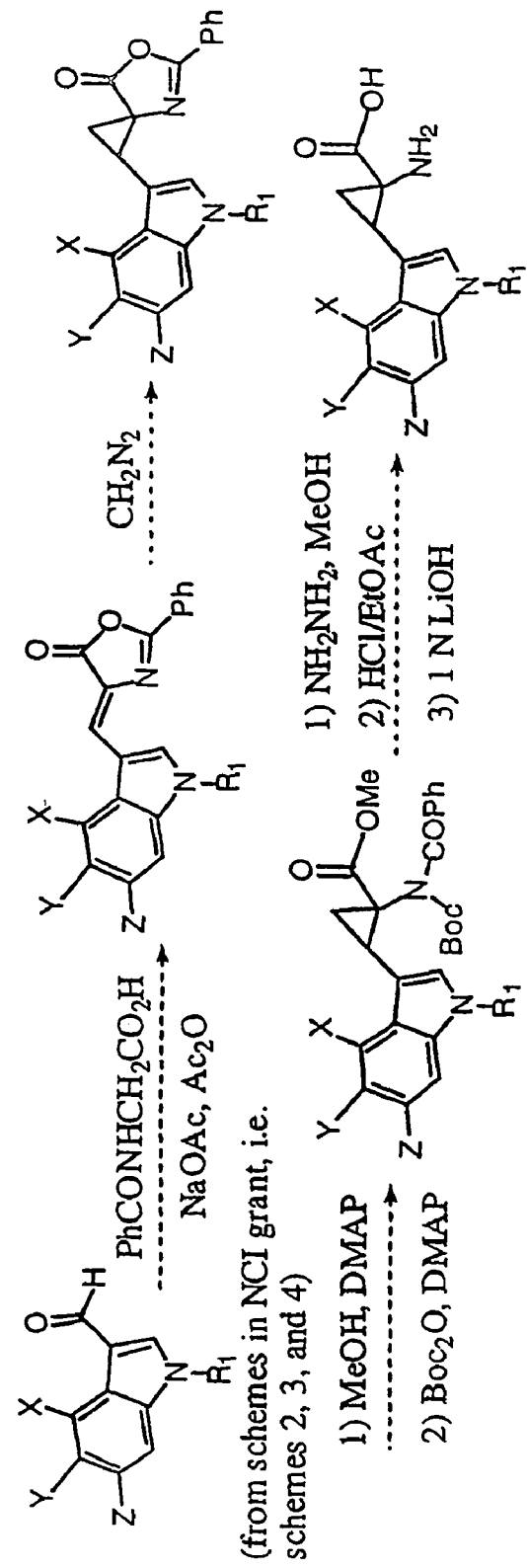
FIG. 16 provides a scheme for synthesizing cyclopropyl tryptophan derivatives of the present invention.
Figure 17:
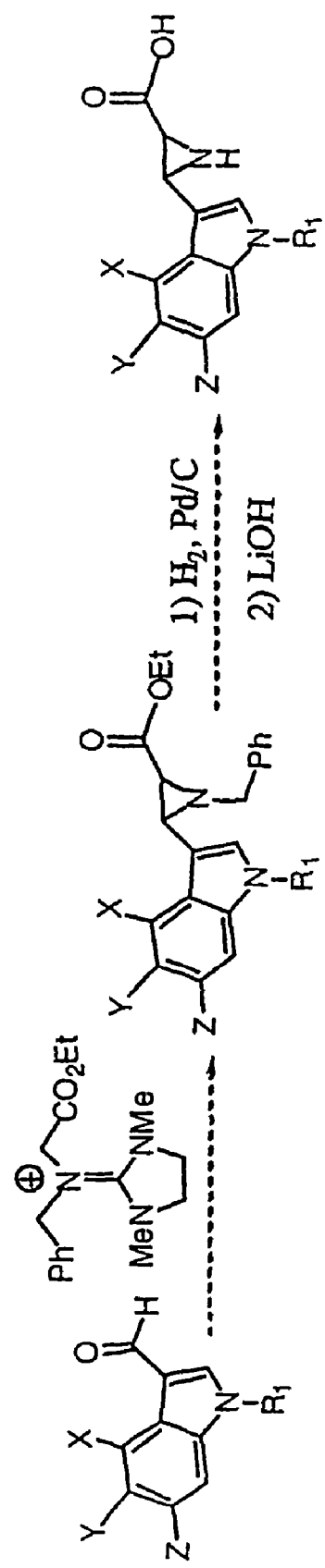
FIG. 17 provides a scheme for synthesizing aziridinyl tryptophan derivatives of the present invention.

The schemes for synthesizing cyclopropyl/aziridinyl tryptophan derivatives, compounds of formula (I) where $R_3$ is (c) or (d), are shown in FIGS. 16 and 17 (see, for example, Donati et al. (1996) Tetrahedron 52:9901-9908; Ishikawa et al. (2001) J. Am. Chem. Soc. 123:7705-7706).

Example 7

Synthesis of Tethered Competitive/Noncompetitive Derivatives

Figure 18:
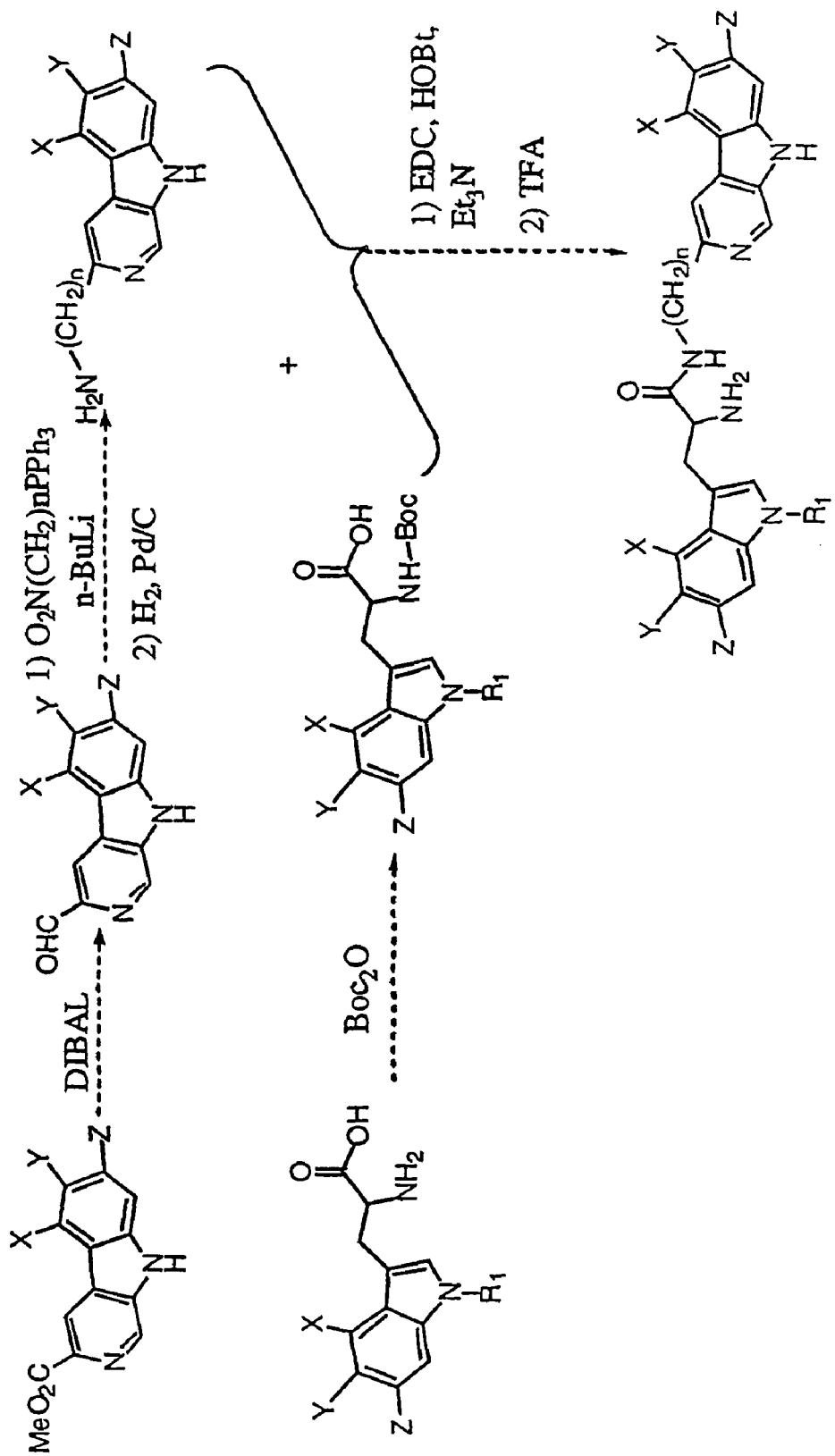
FIG. 18 provides a scheme for synthesizing tethered competitive/noncompetitive derivatives of the present invention.

FIG. 18 shows the scheme for the synthesis of tethered competitive/noncompetitive derivatives, i.e. compounds of formula (I) where $R_3$ is (e).

Example 8

Synthesis of Didehyro Derivatives

FIG. 1 shows a scheme for the synthesis of didehydro derivatives (compound 3 in FIG. 1), i.e. compounds of formula (I) where $R_3$ is (f). Example 1 hereinabove provides a more detailed description of these compounds. Notably, both E and Z diastereomers are included in the instant invention.

Example 9

Evaluation of Novel IDO Inhibitors

1. Biochemical Evaluation of Novel IDO Inhibitors:

Overview: The biochemistry of IDO is well established, the enzyme having first been isolated in 1963 (Higuchi, K., et al. (1963) Federation Proc. 22:243 (abstr.); Shimizu, T., et al. (1978) J. Biol. Chem. 253:4700-6). IDO is a monomeric, haem-containing oxidoreductase with a molecular weight of approximately 41 kDa. To maintain the active ferrous form during in vitro catalysis, the enzyme requires methylene blue in combination with either superoxide or a reductant such as ascorbic acid. In vivo, it is suggested that a flavin or tetrahydrobiopterin may fulfill the role of the methylene blue dye and that there is likely to be a specific site for noncompetitive IDO inhibitors. Active enzyme can be produced by expressing the cloned, His-tagged version of the mammalian gene in bacteria (Littlejohn, T. K., et al. (2000) Prot. Exp. Purif. 19:22-29). This provides a convenient source of enzyme for biochemical analysis. A conventional biochemical assay for IDO activity based on spectaphotometric measurement of the production of kynurenine (the hydrolysis product of N-formyl-kynurenine) from tryptophan (Daubener, W., et al. (1994) J. Immunol. Methods 168:39-47) is used as the read-out for both the enzymatic and cell-based assays. The enzymatic assay provides a facile, high-throughput screen for identifying compounds with IDO inhibitory activity. This assay is also used to determine Ki values for specific compounds, which is important for the development of SAR (structure activity relationship) around the different compound series. The cell-based assay both confirms the IDO inhibitory activity of identified compounds, and addresses the initial issue of bioavailability—the ability of compounds to inhibit intracellular IDO. Specificity for IDO inhibition is examined in the cell-based assay by comparing against the other known tryptophan catabolizing enzyme tryptophan dioxygenase (TDO, also referred to in the literature as TDO2).

Figure 19A:
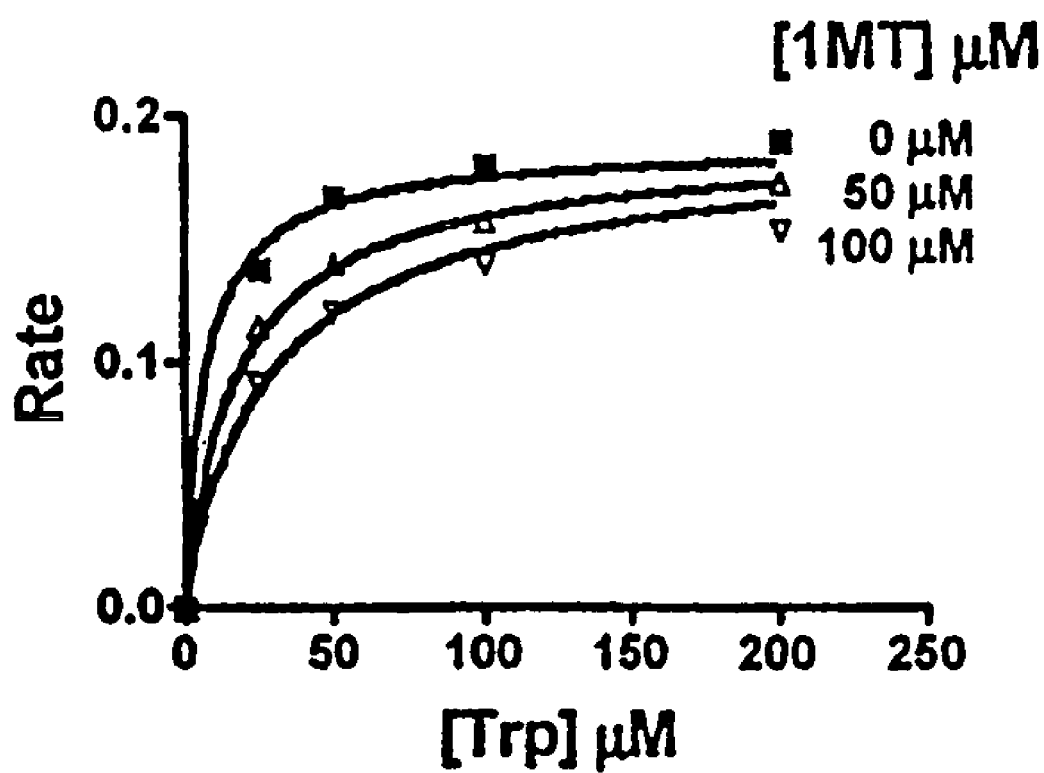
FIGS. 19A and 19B are graphs showing the results of an enzyme assay for IDO inhibitors. Global nonlinear regression analysis of enzyme kinetic data was obtained for human IDO in the presence of increasing concentrations of A) 1MT and B) MTH-Trp. Data were plotted and analyzed using the Prism4 software package (GraphPad). Best fit values of Ki for 1MT=34.6 μM and for MTH-Trp=11.4 μM
Figure 19B:
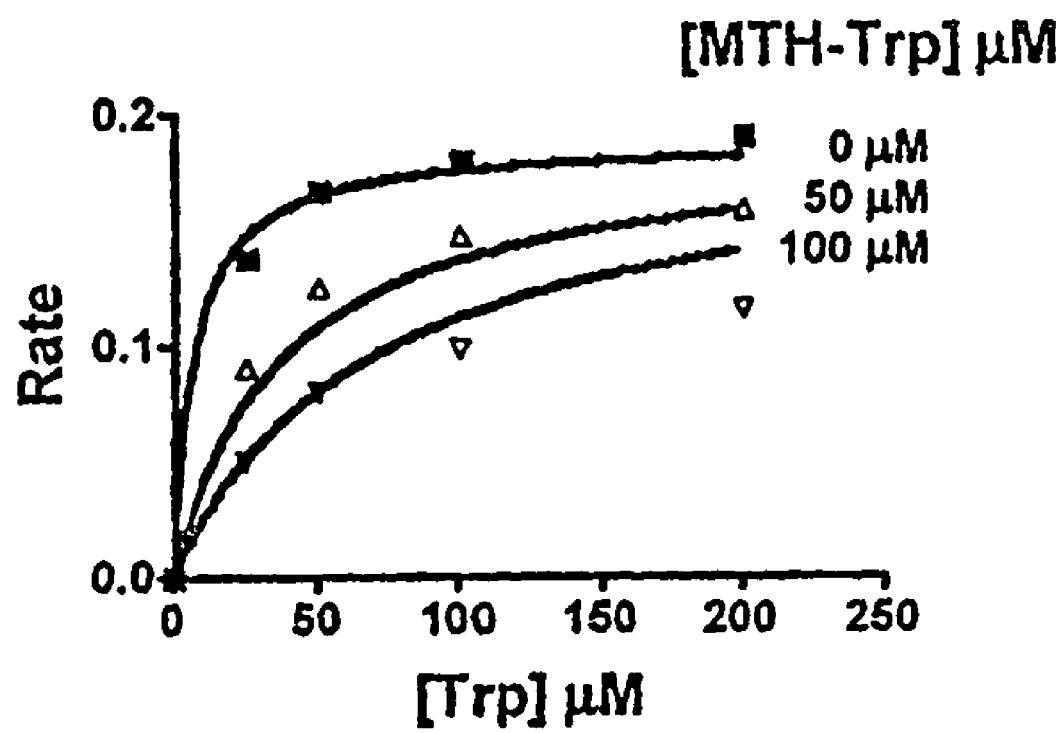

Methods: cDNA clones for both human and mouse IDO have been isolated and verified by sequencing. To prepare enzyme for biochemical studies, C-terminal His-tagged IDO protein can be produced in *E. coli* using the IPTG-inducible pET5a vector system and isolated over a nickel column. The yield of the partially purified protein can be verified by gel electrophoresis and the concentration estimated by comparison to protein standards. To assay IDO enzymatic activity, a 96-well plate spectraphotometric assay for kynurenine production can be run following published procedures (Littlejohn, T. K., et al. (2000) Prot. Exp. Purif. 19:22-29; Takikawa, O., et al. (1988) J. Biol. Chem. 263:2041-8). To screen for evidence of IDO inhibitory activity, compounds can be evaluated at a single concentration of, for example, 200 µM against 50 ng of IDO enzyme in 100 µl reaction volumes with tryptophan added at increasing concentrations at, for example, 0, 2, 20, and 200 µM. Kynurenine production can be measured at 1 hour. More extensive enzyme kinetic data can be collected for selected compounds of interest. Best fit Ki value determinations for 1 MT (Ki=34.6 µM) and for MTH-Trp (Ki=11.4 µM) are shown in FIG. 19. These data indicate that the thiohydantoin form directly inhibits IDO enzyme activity with about 3-fold greater potency than is achieved with 1 MT.

Figure 20:
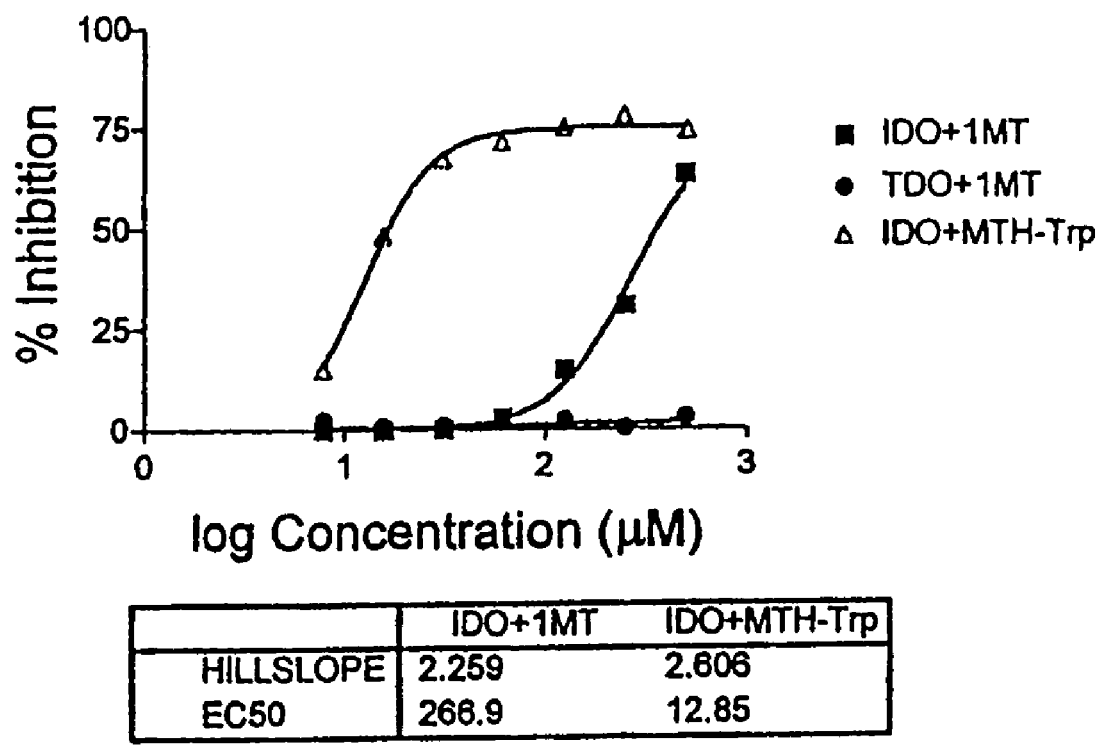
FIG. 20 is a graph showing the result of a cell-based IDO inhibitor assay of 2 log dose escalation studies for 1 MT against IDO, 1 MT against TDO, and MTH-Trp against IDO. Data were plotted using the Prism4 data analysis program (GraphPad), and Hillslope and EC50 values were determined by nonlinear regression analysis.

The following procedure is an example of a cell-based assay. COS-1 cells are transiently transfected with a CMV promoter-driven plasmid expressing IDO cDNA using Lipofectamine 2000 (Invitrogen) as recommended by the manufacturer. A companion set of cells is transiently transfected with TDO-expressing plasmid. 48 hours post-transfection, the cells are apportioned into a 96-well format at $6 \times 10^4$ cells per well. The following day the wells are washed and new media (phenol red free) containing 20 µg/ml tryptophan is added together with inhibitor. The reaction is stopped at 5 hours and the supernatant removed and spectraphotometrically assayed for kynurenine as described for the enzyme assay (Littlejohn, T. K., et al. (2000) Prot. Exp. Purif. 19:22-29; Takikawa, O., et al. (1988) J. Biol. Chem. 263:2041-8). To obtain initial confirmation of IDO activity, compounds can be evaluated at a single concentration of, for example, 100 µM. More extensive dose escalation profiles can be collected for select compounds. EC50 value determinations for 1 MT (EC50=267 µM) and for MTH-Trp (EC50=12.9 µM) are shown in FIG. 20. These data indicate that MTH-Trp is substantially more potent against intracellular IDO (~20-fold) than is 1MT.

Figure 21:
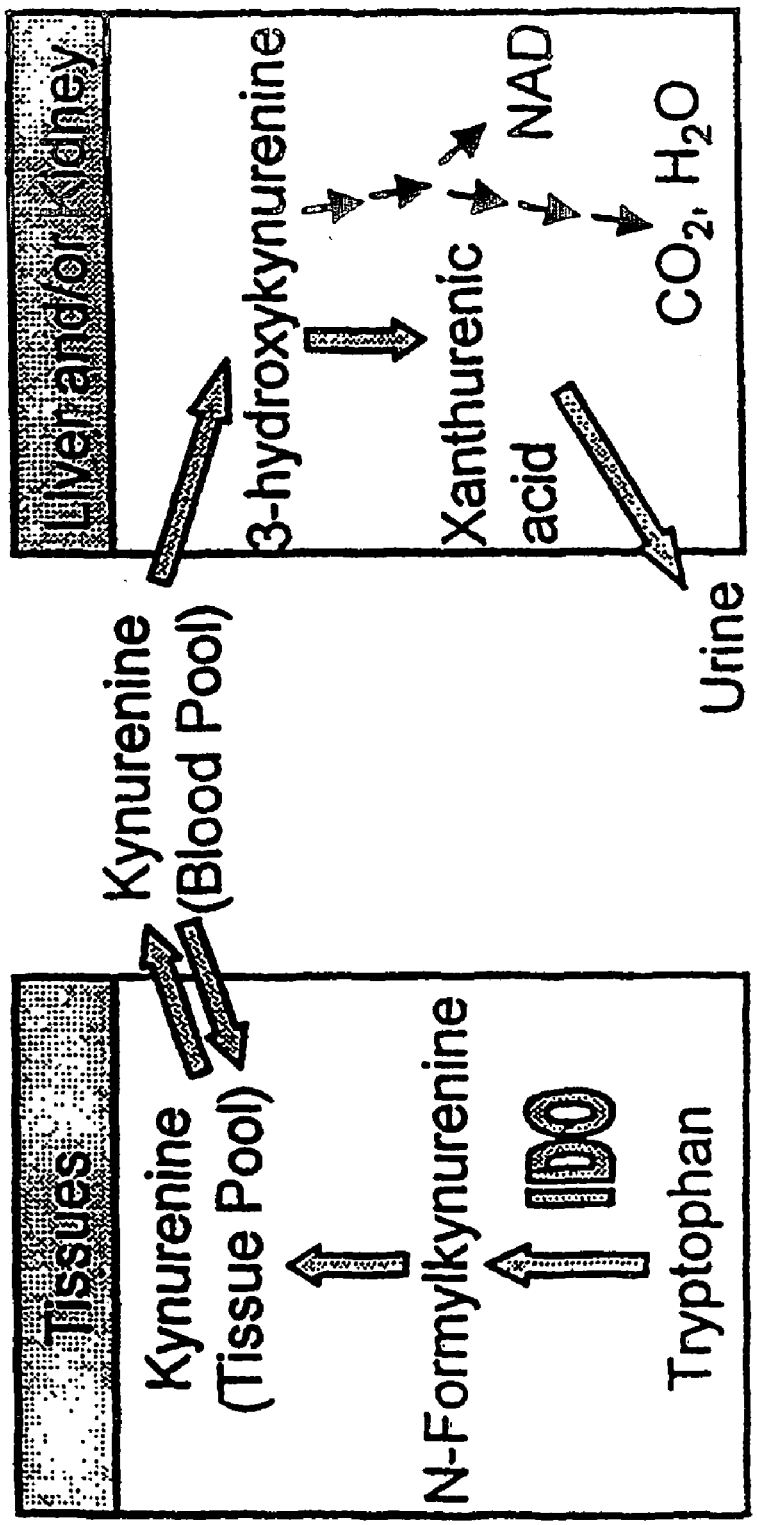
FIG. 21 is a schematic diagram of the kynurenine metabolism pathway. IDO is an extrahepatic, interferon-γ inducible oxidoreductase. The product of the IDO reaction, N-formylkynurenine is rapidly hydrolyzed to kynurenine. Kynurenine is distributed between tissue and blood spaces because there is little or no activity of the enzymes that further metabolize kynurenine in tissues. The major route of kynurenine clearance is excretion in urine after conversion to xanthurenic acid in the liver and/or kidneys, although it is also an intermediate in the biosynthetic pathway that produces nicotinamide adenine dinucleotide (NAD) (Takikawa et al. (1986) J. Biol. Chem. 261:3648-3653; Thomas and Stocker (1999) Redox. Report 4:199-220).

2. Pharmacodynamic/Pharmacokinetic Evaluation of Novel IDO Inhibitors:

Overview: Intraperitoneal administration of bacterial lipopolysaccharide (LPS) induces IDO activity in a variety of tissues resulting in the production of kynurenine and its release into the bloodstream (FIG. 21). Peak kynurenine levels are reached one day after LPS administration (Takikawa, O., et al. (1986) J. Biol. Chem. 261:3648-53; Yoshida, H., et al. (1998) Cell 94:739-750). The pharmacodynamic assay described here is based on measuring serum levels of both kynurenine and tryptophan. Calculating the kynurenine/tryptophan ratio provides an estimate of IDO activity that is independent of baseline tryptophan levels (Fuchs, D., et al. (1991) Immunol. Lett. 28:207-11; Gasse, T., et al. (1994) Eur. J. Clin. Chem. Clin. Biochem. 32:685-9), and this approach to measuring IDO activity has been used frequently in humans. The principle advantage of this approach over the direct assessment of IDO enzymatic activity in tissue is that it is a non-invasive procedure permitting multiple samples to be collected from the same animal. This enables IDO activity to be monitored in a single mouse at multiple time points. Tryptophan and kynurenine levels in the serum can be determined by HPLC analysis. The level of compound in serum can also be determined in the same HPLC run, thus permitting concurrent collection of pharmacokinetic data in a single experiment.

Methods: FVB MMTV-neu male mice at ~8-10 weeks of age can be used to perform the bulk of the pharmacodynamic analysis because their genetic background is the same as that of the MMTV-neu females mice that are used in the mammary gland tumor model to evaluate compound efficacy. *Salmonella minnesota* mutant strain R-595 (*S. minnesota* R) derived LPS has been shown to elicit the most sustained level of kynurenine induction in a comparative analysis of LPS preparations from different bacterial strains (Yoshida, R., et al. (1981) Arch. Biochem. Biophys. 212:629-37). Because it provides the widest window in which to evaluate the impact of IDO inhibitors, this preparation of LPS can be used in the pharmacodynamic assay. The minimum i.p. bolus dose of *S. minnesota* R LPS that elicits maximal IDO activity has been reported to be ~1 mg/kg and maximal IDO activation is reached by ~24 hr. following LPS treatment (Yoshida, R., et al. (1981) Arch. Biochem. Biophys. 212:629-37).

Figure 22:
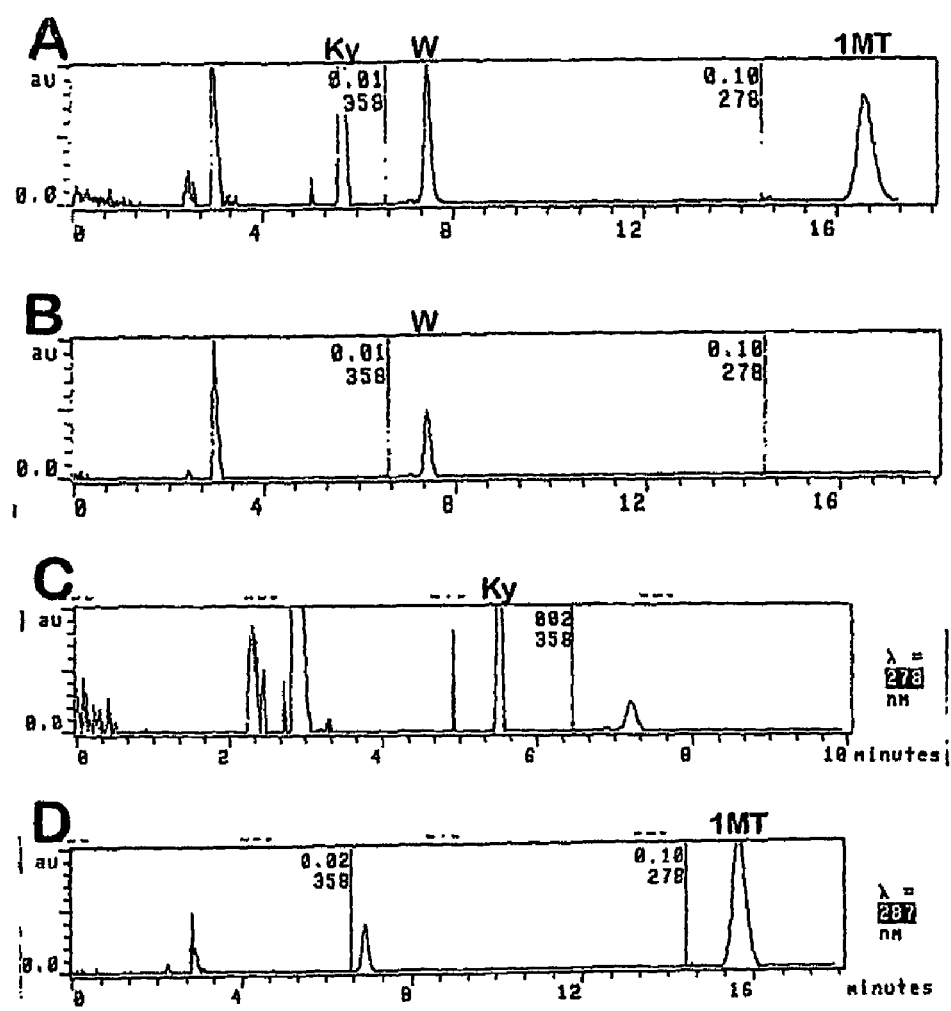
FIGS. 22A-D are chromatograms showing the results of HPLC analysis of mouse serum. Serum was prepared by incubating collected blood samples at 4° C. overnight and removing the clot. Protein was removed by TCA precipitation. Samples were resolved on a 250 mm×4.5 mm Luna 5μ C18 column (Phenomenex) in isocratic buffer consisting of 20% MeOH, 5% acetonitrile, 10 mM $KPO_4$ (pH 5.3), 0.15 mM EDTA. Serum samples were prepared from male FVB strain mice treated as follows: A) Untreated (serum was spiked with 30 μM each of the following control compounds; tryptophan, kynurenine, and 1MT); B) Untreated (55 μM serum tryptophan is detectable); C) LPS challenged for 24 hrs. (induction of kynurenine to 5.6 μM is detectable), D) 1MT pellets implanted subcutaneously for 3 days (104 μM 1 MT is detectable). Output sensitivity (Y-axis) has been adjusted at 6.66 and 14.5 minutes to optimize for each anticipated peak height. Ky=kynurenine, W=tryptophan, 1 MT=1-methyl-tryptophan.

Serum levels of kynurenine and tryptophan can be quantitatively determined by HPLC analysis (Hwu, P., et al. (2000) J Immunol 164:3596-9; Widner, B., et al. (1997) Clin. Chem. 43:2424-6; see FIGS. 22A-D). By this procedure, serum concentrations of at least 1.25 µM kynurenine and 3 µM tryptophan are detected. In unchallenged FVB male mice the serum kynurenine is at or below the limit of detection and serum tryptophan is readily detectable at ~50 µM (FIG. 22B). 24 hr after LPS challenge, serum kynurenine is induced to ~6 µM (FIG. 22C). 1 MT in serum at a concentration of at least 5 µM can also be effectively measured. This is well below the serum levels of ~100 µM 1 MT achieved with biologically efficacious dosing of 2×140 mg 1 MT pellets (FIG. 22D).

Compounds can be evaluated first by challenging with LPS and then subsequently administering a bolus dose of compound at the time that the serum kynurenine level plateaus. The kynurenine pool is rapidly turned over with a half-life in serum of less than 10 minutes (Bender, and McCreanor (1982) Biochim. Biophys. Acta 717:56-60; Takikawa, O., et al. (1986) J. Biol. Chem. 261:3648-53) so that pre-existing kynurenine is not expected to unduly mask the impact that IDO inhibition has on kynurenine production. The vehicle chosen for administration can depend in large part on the physical properties of each particular compound. The preferred vehicle is isotonic saline, but this requires that the compound be soluble in aqueous solution. It is anticipated that some compounds may not be sufficiently soluble, in which case the compounds can be administered as a suspension in Methocel®/Tween® (0.5% methylcellulose/1% Tween® 80).

Each experiment can include non-LPS-exposed mice (to determine baseline kynurenine levels against which to compare the other mice) and a set of LPS-exposed mice dosed with vehicle alone (to provide a positive control for IDO activation). Mice can be monitored following LPS administration and immediately euthanized if they present with signs of pronounced endotoxemia (ruffled fur, sluggishness). Each compound can initially be evaluated in mice at a single high i.p. bolus dose in the range of at least 100 mg/kg. Blood can be collected at defined time intervals (for example, 50 µl/sample at 5, 15, 30 min., 1, 2, 4, 6, 8, and 24 hr. following compound administration) for HPLC analysis of kynurenine and tryptophan levels (pharmacodynamic analysis) as well as for the level of compound (pharmacokinetic analysis). From the pharmacokinetic data the peak serum concentration of compound achieved can be determined as well as the estimated rate of clearance. By comparing the level of compound in serum relative to the kynurenine/tryptophan ratio at various time points, the effective $IC_{50}$ for IDO inhibition in vivo can be roughly estimated.

Based on the results of the single dose study, a second dose escalation study can be conducted for every efficacious compound. The study can be, for example, aimed at a maximum dose that achieves 100% IDO inhibition at the peak concentration (if possible) in one cohort of mice and dose additional cohorts with concentrations that decrease in 3-fold stepwise increments to cover a 2 $\log_{10}$ range between the highest and lowest doses. Accurate $IC_{50}$ determinations can be extracted from these data. The same approach can be used to test for oral bioavailability of biologically active compounds, first testing each compound at a single maximum concentration p.o. bolus dose and then further evaluating those compounds that exhibit significant oral efficacy in a dose escalation study. To ensure that in vivo responsiveness is not subject to sexual dimorphism, a single i.p bolus dose experiment can be carried out in female mice at the calculated $IC_{50}$ dose for each active compound.

Example 10

Combinatorial Treatment of Tumors with an IDO Inhibitor and a Signal Transduction Inhibitor The MMTVneu transgenic "oncomouse" model of breast cancer was used to measure the effects of IDO inhibitors and STIs on tumor pathophysiology. The MMTVneu transgenic mouse develops aggressive tumors of the mammary gland that resemble poorly differentiated human ductal carcinomas. In the MMTVneu mouse model, breast cancer is initiated by tissue-specific expression of a mutant form of the HER-2/Neu gene that is activated frequently in aggressive human breast ductal carcinomas. HER-2 is a member of the EGF-R family of cell surface growth factor receptors. Myc is an obligate downstream effector for HER-2/Neu to drive cancer. Female MMTVneu "oncomice" are mated twice to initiate expression from the mouse mammary tumor virus (MMTV) promoter which drives transcription of the Neu/HER2 oncogene in mammary tissue. Mammary tumors arise with a penetrance of >90% in this model system by 5 months of age. MMTVneu "oncomice" bearing similarly sized tumors of ~150 $mm^3$ were randomly assigned to control or experimental treatment groups. Control mice were implanted with placebo time-release pellets (Innovative Research, Inc., Sarasota, Fla.). Experimental groups of mice were (1) implanted with 1 MT-containing time-release pellets, (2) treated with L-744,832, or (3) implanted with 1MT-containing time-release pellets and treated with L-744,832. L-744,832, which mimics the CaaX motif to which the farnesyl group is added, is a potent and selective inhibitor of farnesyl transferase (FTI) (Kohl et al., (1995) Nat Med. 1(8):747-748).

The time-release pellets are composed of a copolymer which is inert and gradually dissolves and breaks down to a non-toxic substance that remains largely localized during the course of the experiment. Time-release pellets impregnated with 1MT release a dose of 10 mg/day for a period of up to 14 days as documented by the commercial vendor (Innovative Research, Inc., Sarasota, Fla.). Two pellets per mouse were implanted to deliver a total dose of 20 mg/day. Therefore, for a 25 g mouse the total dose is 800 mg/kg/day or 280 mg over a 14 day period. Steady-state levels were reached within 12-24 hours and are maintained throughout the entire period based on the manufacturer's specifications. The delivered dose is effective at eliciting allogenic conceptus rejection (A. Muller, J. B. DuHadaway, G. C. Prendergast, unpublished results) as described by Munn et al. (Science 281:1191-1193, 1998).

Time-release pellets were introduced subcutaneously on the backs of mice anesthetized by intramuscular injection of ketamin/rompun. Blunt dissection with a hemostat is used to separate the skin from the underlying muscle to create a subcutaneous pocket. One or two biodegradable slow release pellets were implanted within this pocket, rather than directly under the incision in order to prevent mechanical stress and wound dehiscence. The incision was then closed with wound clips. Based on the ability of female mice that have been implanted with placebo time-release pellets to carry pregnancies to term, distress from the procedure appears to be negligible.

The signal transduction inhibitors, e.g., FTI L-744,832 were prepared and delivered to the mice as described in Kohl et al. (Nature Med. (1995) 1:792-797).

Figure 23:
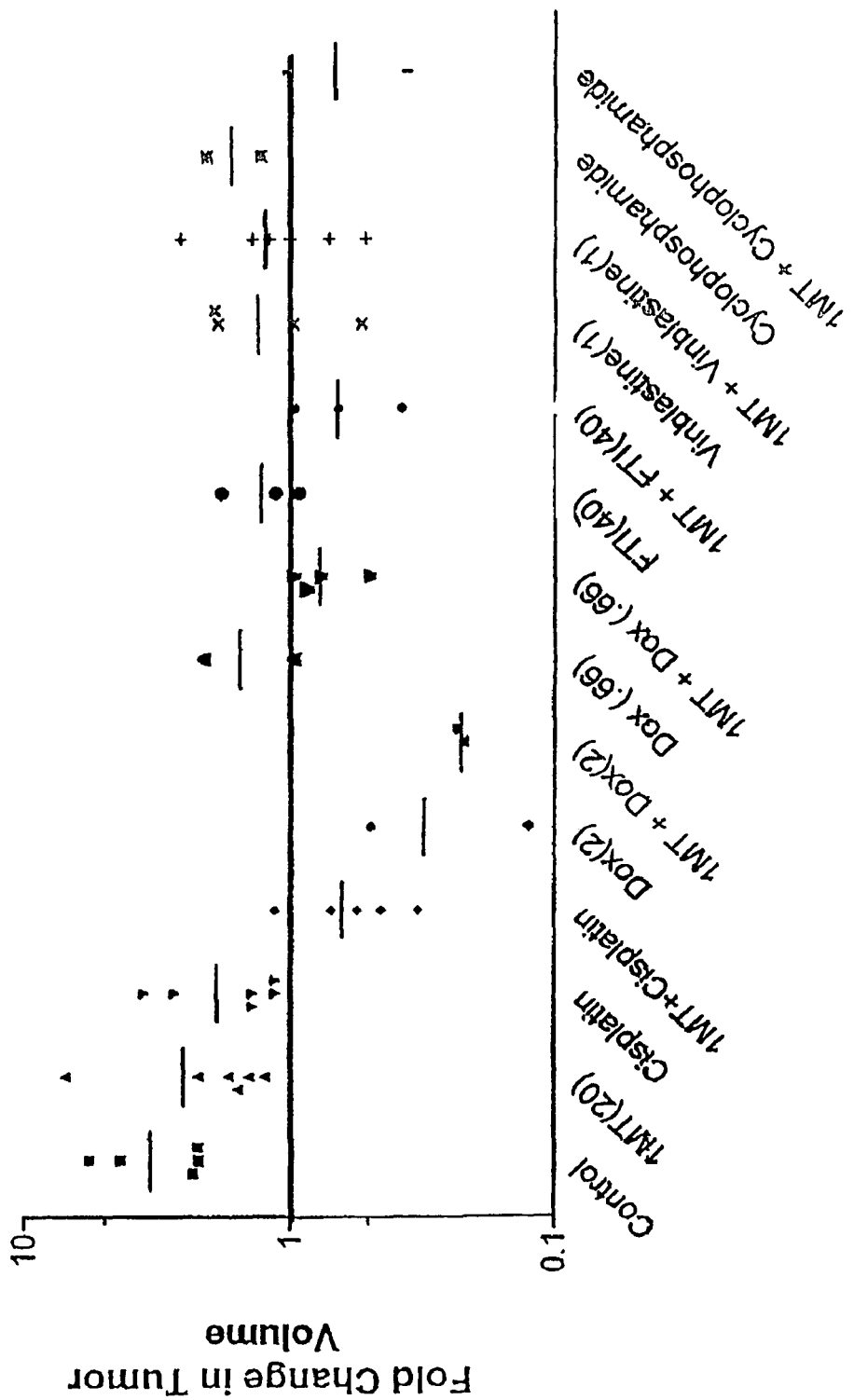
FIG. 23 is a graph illustrating the fold change in tumor volume of MMTVneu mice either mock treated (untreated) or treated with 1 MT, L-744,832 (FTI), 1MT and L-744,832, and chemotherapeutic agents with or without 1MT. Each data point was determined from an individual mouse and the bars indicate the mean of the data points as listed at the bottom of the graph.

FIG. 23 summarizes the findings of the experiments to test the ability of 1MT to cooperate with FTI L-744,832 (as well as chemotheraeutic agents) to cause regression of established tumors in MMTVneu "oncomouse" model. During the two week course of the experiment, an elevation of ~200% in the tumor volume of mock-treated control mice was observed. Treatment of mice with 20 mg/day 1MT, delivered by subcutaneous time-release pellets, retarded but did not block tumor growth. Similarly, treatment of tumor-bearing mice with FTI L-744,832 retarded but did not block tumor growth. In contrast, the combination of 1MT plus L-744,832 treatment caused tumor regression in the model.

Example 11

Assaying Novel IDO Inhibitors

A variety of compounds were screened for their efficacy as IDO inhibitors. Certain compounds were screened in a biochemical assay as follows. IDO cDNAs were expressed in bacteria as his-tagged proteins and purified as previously described (Littlejohn et al. (2000) Prot. Exp. Purif. 19:22-29). Briefly, the purified IDO was incubated with substrate and varying amounts of the IDO inhibitor candidate. The fluorescence of the reaction mixture was measured to determine the efficacy of the candidate inhibitor because a product of the reaction, kynurenine, is fluorescent. The results of the in vitro biochemical screen are depicted in FIG. 24.

The candidate compounds were also screened in a cell-based assay (for similar assay see Munn et al. (1999) J. Exp. Med. 189:1363-1372). Briefly, human 293/Phoenix cells were transiently transfected with human IDO or TDO cDNA expression vectors. The candidate compounds were added to the transfected cells at various concentrations. Kynurenine was quantitated in tissue culture media using a fluorescence-based protocol. The results from these experiments are presented in FIGS. 25-27.

Figure 26:
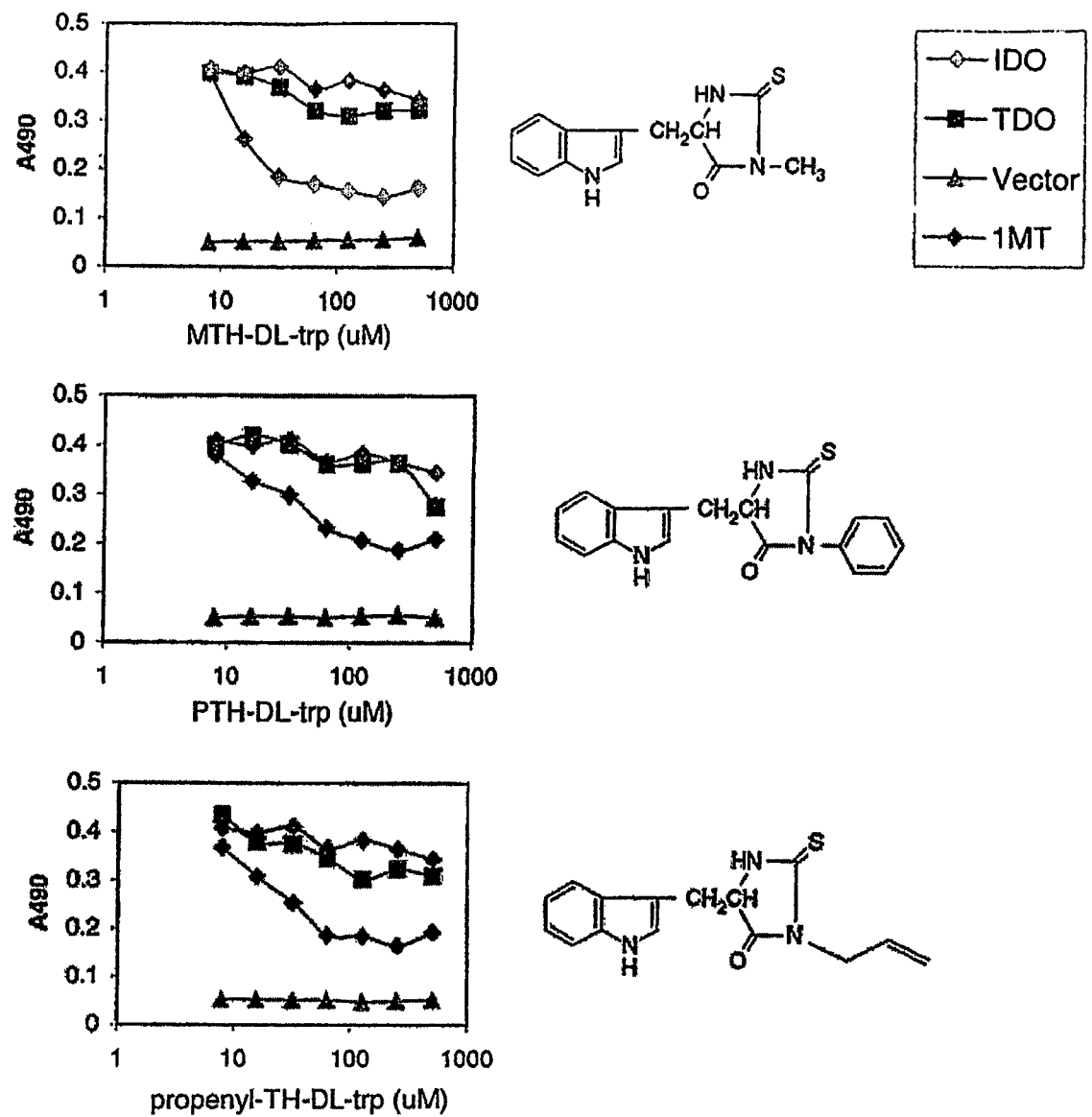
FIG. 26 provides graphs of the thiohydantoin derivatives of indoleamine in the cell-based assay for screening of IDO inhibitor candidates. The cells were transfected with empty expression vectors (vector) or with expression vectors which contain IDO or TDO. For comparison, cells transfected with the IDO expression vector were also assayed in the presence of 1 MT.

As noted in these figures, the most potent inhibitors identified are a set of thiohydantoin derivatives of indoleamine. FIG. 26 provides results using these particular inhibitors. The most potent of these inhibitors, methyl-TH-DL-trp, displayed an inhibition of IDO activity 2.7 times greater than 1MT at a concentration of 250 µM (FIG. 27).

Figure 25B:
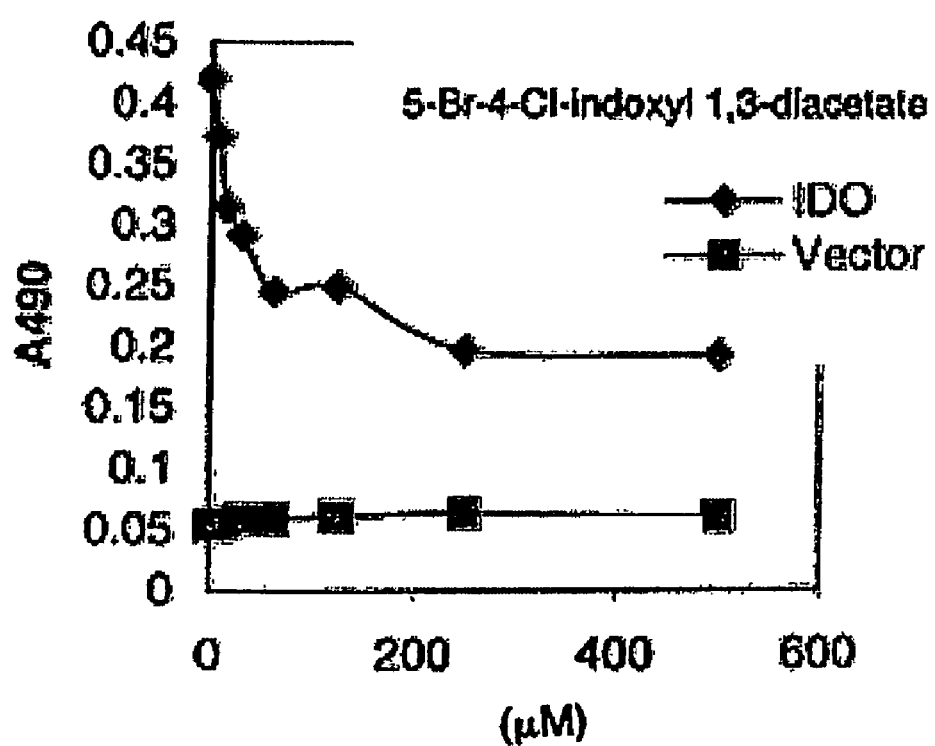

In addition to the thiohydantoin derivatives of indoleamine, a group pf natural products was screened. Interestingly, effective inhibitors from this group were compounds from foods with cancer preventitive properties (e.g. cruciferous vegetables). Brassinin, a compound found in Chinese cabbage, was scored as the most potent compound among the natural products determined to be IDO inhibitors (FIG. 25A).

The toxicity of certain screened compounds was also examined. As seen in FIG. 28, most IDO inhibitory compounds are not intrinsically growth inhibitory or cytotoxic to neoplastically transformed breast or prostate cancer cells (FIG. 28).

Example 12

Combinatorial Treatment of Tumors with an IDO Inhibitor and Cytotoxic Chemotherapeutic Agent The MMTVneu transgenic "oncomouse" model of breast cancer was also used to measure the effects of IDO inhibition and cytotoxic chemotherapeutic agents on tumor pathophysiology.

MMTVneu "oncomice" bearing similarly sized tumors of ~150 mm$^3$ were randomly assigned to control or experimental treatment groups. Control mice were implanted with placebo time-release pellets (Innovative Research, Inc., Sarasota, Fla.). Experimental groups of mice were (1) implanted with 1 MT-containing time-release pellets as described in Example 10, (2) treated with paclitaxel (Taxol®) or other cytotoxic agents, or (3) implanted with 1MT-containing time-release pellets and treated with paclitaxel or other cytotoxic agents.

Time-release pellets were introduced subcutaneously on the backs of mice as described previously.

The cytotoxic chemotherapeutic agents were prepared and delivered to the mice as follows. Paclitaxel was dissolved in equal volumes of absolute ethanol and the clinically-used solubilizing agent Cremophor® EL. The solution was sonicated up to 30 minutes and stored as a 20 mg/ml stock solution at 4° C. for up to one week. Before use, this solution was diluted further at 1:5 with sterile physiological saline. Paclitaxel formulated in this manner was administered to mice by a single bolus intravenous (i.v.) injection into the tail vein. Mouse tails can be warmed to facilitate identification and injection of the vein. The maximum tolerated dose (MTD) of paclitaxel (13.3 mg/kg) was delivered five (5) times during the 2 week experiment on a thrice-weekly schedule (i.e., Friday—pellet implantation; Monday/Wednesday/Friday, Monday/Wednesday—paclitaxel inject; Friday—euthanize animals and harvest tumors for analysis). The MTD of cisplatin (1 mg/kg) was obtained as a clinical preparation in saline and delivered as a bolus i.v. injection on the same schedule. Control treated mice received only the Cremophor® EL vehicle formulation without paclitaxel.

Figure 29:
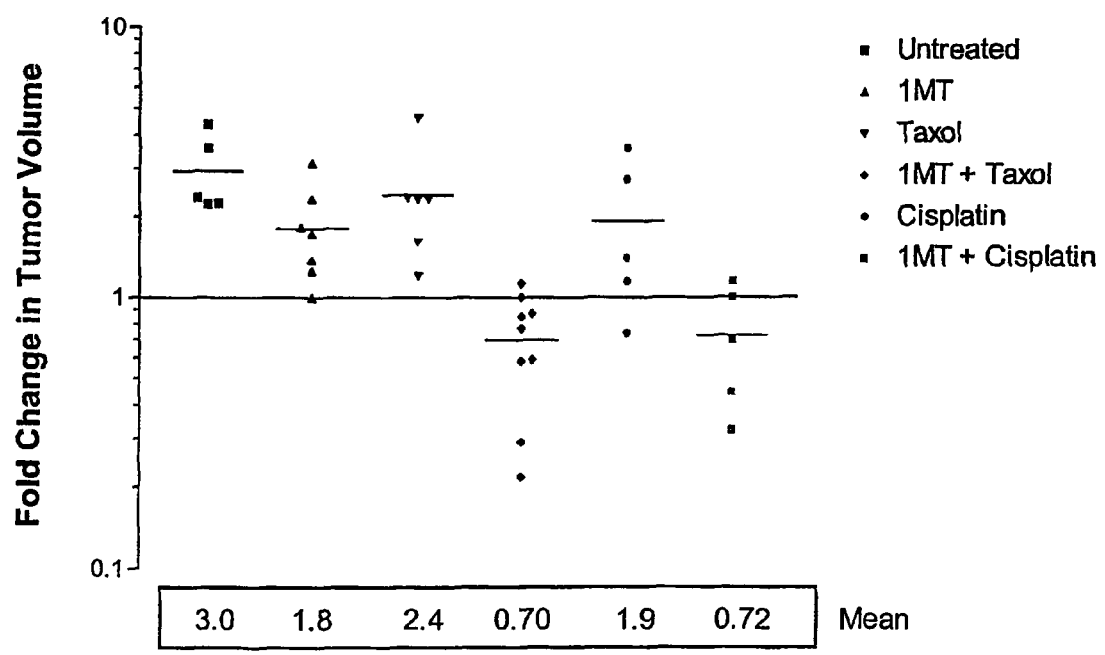
FIG. 29 is a graph illustrating the fold change in tumor volume of MMTVneu mice either mock treated (untreated) or treated with 1MT, paclitaxel (Taxol®), 1MT and paclitaxel (Taxol®), cisplatin, or 1MT and cisplatin. Each data point was determined from an individual mouse and the bars indicate the mean of the data points as listed at the bottom of the graph.

FIG. 29 and Table 1, in addition to FIG. 23, summarize the findings of the experiments to test the ability of 1MT to cooperate with two cytotoxic agents to cause regression of established tumors in MMTVneu "oncomouse" model. During the two week course of the experiment, an elevation of ~200% in the tumor volume of mock-treated control mice was observed. Treatment of mice with 20 mg/day 1 MT, delivered by subcutaneous time-release pellets, retarded but did not block tumor growth. Similarly, treatment of tumor-bearing mice by intravenous injection of paclitaxel or cisplatin at the maximum-tolerated doses retarded but did not block tumor growth. In contrast, the combination of 1 MT plus paclitaxel or cisplatin treatment caused tumor regression in the model. Similar results were observed with a reduction of paclitaxel to ~25% the maximum-tolerated dose (data not shown). Inasmuch as the cytotoxic agents employed in these studies are known to be toxic to the very T cells that the IDO inhibitors would allow to be recruited and activated, these results are unexpected in view of the prior art.

TABLE 1

|  | Untreated | 1MT only | Taxol only | 1MT + Taxol | Cisplatin only | 1MT + Cisplatin |
| --- | --- | --- | --- | --- | --- | --- |
| Number of Mice | 5 | 5 | 5 | 6 | 3 | 3 |
| Number of Tumors | 5 | 7 | 6 | 9 | 5 | 5 |
| Mean | 195.1 | 80.27 | 139.4 | −30.2 | 91.35 | −27.94 |
| Std. Deviation | 97.54 | 73.12 | 118.1 | 30.7 | 118.5 | 35.1 |
| Std. Error | 43.62 | 27.64 | 48.2 | 10.23 | 53 | 15.7 |
| Minimum | 122.2 | 0 | 20 | −78.4 | −26.53 | −67.86 |
| 25% Percentile |  | 25 | 40.25 | −56.5 |  |  |
| Median | 134.4 | 72.87 | 130.4 | −23.44 | 40 | −30.56 |
| 75% Percentile |  | 130.4 | 247.6 | −6.445 |  |  |
| Maximum | 336.5 | 215 | 360.8 | 12.5 | 255.6 | 14.29 |
| Lower 95% CI | 73.95 | 12.65 | 15.52 | −53.8 | −55.79 | −71.52 |
| Upper 95% CI | 316.2 | 147.9 | 263.3 | −6.605 | 238.5 | 15.64 |

Statistical analysis of the tumors of MMTVneu mice after various treatments. Numbers are provided as percent change in tumor volume as compared to the tumor volume prior to treatment. Lower and upper 95% Cl indicate lower and upper 95% confidence limits.

Histological and immunohistochemical analysis of tumor sections isolated from the control and experimental cohorts revealed dramatic changes only in the tumor tissues from the mice treated with the combinatorial regiment. Most notably, evidence of pronounced hemorrhage, apoptosis, and infiltration of CD3-positive T cells was seen in the mice that received the combinatorial regiment (data not shown). In conclusion, the combined application of 1 MT with cytotoxic agents was efficacious in eliciting regression of established breast tumors in the MMTVneu "oncomouse" model system.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

Several publications and patent documents are cited in the foregoing specification in order to more fully describe the state of the art to which this invention pertains. The disclosure of each of these citations is incorporated by reference herein.

What is claimed is:

1. A compound having indoleamine 2,3 dioxygenase (IDO) inhibitory activity, said compound having the:

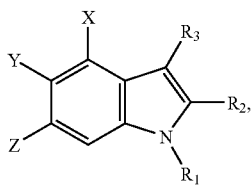
(I)

wherein $R_1$ is H or lower alkyl; $R_2$ and $R_3$ are joined together and represent part of a ring which is fused to the pyrrole moiety of formula (I) and which is selected from the group of:

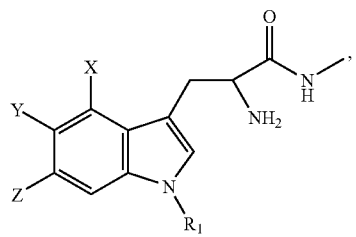
(i)

(ii) wherein $R_E$ is a hydrocarbyl or alkyl-Q, Q representing a substituent of the formula:

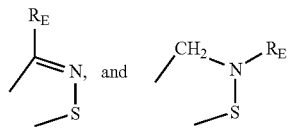

the compound of formula (I) being a brassilexin derivative when $R_2$ and $R_3$ joined together represent (i), and an N-substituted brassilexin derivative when $R_2$ and $R_3$ joined together represent (ii); X, Y, and Z may be the same or different and are selected from the group consisting of H, halogen, $NO_2$, and hydrocarbyl; or Y may also be isothiocyanate.

2. A pharmaceutical composition comprising an effective amount of the compound of claim 1 and a pharmaceutically acceptable carrier medium.

3. A pharmaceutical composition comprising an effective amount of at least one indoleamine 2,3-dioxygenase (IDO) inhibitor and at least one signal transduction inhibitor (STI) in a pharmaceutically acceptable carrier medium, wherein said at least one IDO inhibitor is compounds having the formula:

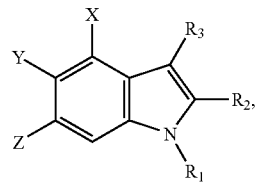
(I)

wherein $R_1$ is H or lower alkyl; $R_2$ and $R_3$ are joined together and represent part of a ring which is fused to the pyrrole moiety of formula (I) and which is selected from the group of:

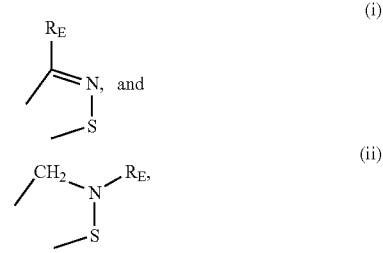
(i)
(ii)

wherein $R_E$ is a hydrocarbyl or alkyl-Q, Q representing a substituent of the formula:

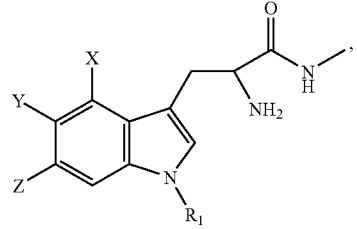

the compound of formula (I) being a brassilexin derivative when $R_2$ and $R_3$ joined together represent (i) and an N-substituted brassilexin derivative when $R_2$ and $R_3$ joined together represent (ii); X, Y, and Z may be the same or different and are selected from the group consisting of H, halogen, $NO_2$, and hydrocarbyl; or Y may also be isothiocyanate.

4. The pharmaceutical composition of claim 3, wherein said at least one STI is selected from the group consisting of bcr/abl kinase inhibitors, epidermal growth factor (EGF) receptor inhibitors, her-2/neu receptor inhibitors, farnesyl transferase inhibitors (FTIs), inhibitors of Akt family kinases or the Akt pathway, and cell cycle kinase inhibitors.

5. The pharmaceutical composition of claim 4, wherein said at least one STI is selected from the group consisting of STI 571, 551-774, C225, ABX-EGF, trastuzumab, L-744, 832, rapamycin, LY294002, flavopiridal, and UNC-01.

6. The pharmaceutical composition of claim 5, wherein said at least one STI is L-744,832.

7. A pharmaceutical composition comprising an effective amount of at least one indoleamine 2,3-dioxygenase (IDO) inhibitor and at least one chemotherapeutic agent in a pharmaceutically acceptable carrier medium, wherein said at least one IDO inhibitor is selected from the group of compounds having the formula:

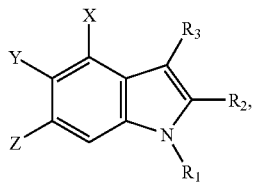
(I)

wherein $R_1$ is H or lower alkyl; $R_2$ and $R_3$ are joined together and represent part of a ring which is fused to the pyrrole moiety of formula (I) and which is selected from the group of:

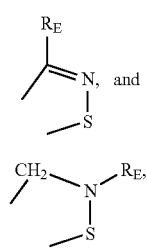

(i)

and (ii)

wherein $R_E$ is a hydrocarbyl or alkyl-Q, Q representing a substituent of the formula:

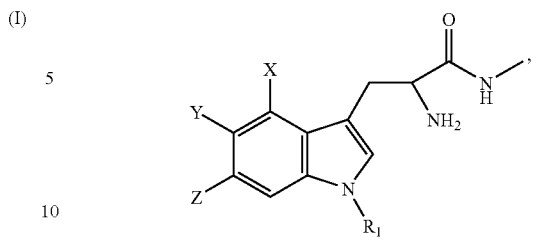

the compound of formula (I) being a brassilexin derivative when $R_2$ and $R_3$ joined together represent (i), and an N-substituted brassilexin derivative when $R_2$ and $R_3$ joined together represent (ii); X, Y, and Z may be the same or different and are selected from the group consisting of H, halogen, $NO_2$, and hydrocarbyl; or Y may also be isothiocyanate.

8. The pharmaceutical composition of claim 7, wherein said at least one chemotherapeutic agent is selected from the group consisting of paclitaxel TAXOL®, cisplatin, docetaxol, carboplatin, vincristine, vinbiastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives.

9. The pharmaceutical composition of claim 4, wherein said at least one chemotherapeutic agent is paclitaxel.

* * * * *